(12) United States Patent
Craig et al.

US007709696B2

(10) Patent No.: US 7,709,696 B2
(45) Date of Patent: May 4, 2010

(54) TRANSGENIC MICE GENERATED BY TRANSPOSITION AND USES THEREOF

(75) Inventors: Roger Craig, Chesire (GB); Charalambos Savakis, Crete (GR); Frank Grosveld, Rotterdam (NL)

(73) Assignees: Erasmus University Medical Center (NL); Minos Biosystems Limited (GB)

( * ) Notice: Subject to any disclaimer, the term of this patent is extended or adjusted under 35 U.S.C. 154(b) by 0 days.

(21) Appl. No.: 10/887,636

(22) Filed: Jul. 9, 2004

(65) Prior Publication Data
US 2005/0066376 A1    Mar. 24, 2005

Related U.S. Application Data

(63) Continuation-in-part of application No. PCT/GB03/00065, filed on Jan. 9, 2003.

(60) Provisional application No. 60/347,107, filed on Jan. 9, 2002.

(51) Int. Cl.
C12N 15/00 (2006.01)
A01K 67/027 (2006.01)

(52) U.S. Cl. .......................... 800/21; 800/18
(58) Field of Classification Search .................. 800/18, 800/21
See application file for complete search history.

(56) References Cited

FOREIGN PATENT DOCUMENTS

WO    WO-00/73510     12/2000
WO    WO 01/71019 A1  9/2001

OTHER PUBLICATIONS

Denning et al. Reproduction 126:1-11, 2003.*
Zagaraiou et al. PNAS 98(20): 11474-11478, 2001.*
Fischer et al. PNAS 98(12): 6759-6764, 2001.*
Horie et al. (PNAS 98(16):9191-9196; 2001.*
Loukeris et al. PNAS 92:9485-9489; 1995.*
vanWert et al. (Biol. Reprod. 59:704-710; 1998).*
O'Gorman et al. PNAS 94:14602-14607; 1997.*
Fischer et al. PNAS 98:6759-6764; 2001.*
International Preliminary Examination Report for PCT/GB03/00065 (Mar. 3, 2004).
Morita Y. et al., "Targeted expression of Bcl-2 in mouse oocytes inhibits ovarian follicle atresia and prevents spontaneous and chemo-therapy-induced oocyte apoptosis in vitro", Mol. Endocrinol., 1999, vol. 13, No. 6, p. 841-850, XPOO2251435.
Rajkovic A. et al., "Functional analysis of oocyte-expressed genes using transgenic models," Mol. Cell Endocrinol., 2002, vol. 187, No. 1-2, p. 5-9. XPOO2251436.
Bartell J.G. et al., "Elimination of male germ cells in transgenic mice by the diptheria toxin A chain gene directed by the histone H1t promoter", Biol. Reprod., 2000, vol. 63, No. 2, p. 409-416. XPOO2251437.
Lira S.A. et al., An upstream region of the mouse ZP-3 gene directs expression of firefly luciferase specifically to growing oocytes in transgenic mice, PNAS, 1990, vol. 87, p. 7215-7219.
Drabent B. et al., "Expression of the mouse histone gene H1t begins at premeiotic stages of spermatogenesis", Cell Tissue Res., 1998, vol. 291, p. 127-132.
Alberts et al., "Molecular Biology of the Cell", 1989, 2nd edition, chap 15 p. 858-859.
Grimes, "Testis-specific transcriptional control", Genes, 2004, vol. 343, p. 11-22.
Drabek et al., "Transposition of the *Drosophila hydei* Minos transposon in the mouse germ line", Genomics, 2003, vol. 81, p. 108-111.

* cited by examiner

*Primary Examiner*—Fereydoun G Sajjadi
(74) *Attorney, Agent, or Firm*—Elizabeth Spar; Kathleen Williams; Edwards Angell Palmer & Dodge LLP

(57) ABSTRACT

A method of inducing transposition in a transgenic embryo, sperm and egg is described, comprising the steps of (a) generating a first adult transgenic organism comprising within its genome one or more copies of a transposon; (b) generating a second adult transgenic organism comprising within its genome one or more copies of a gene encoding a transposase cognate for the transposon and/or a sequence capable of regulating expression of the gene encoding the transposase; (c) crossing the first adult transgenic organism with the second transgenic adult organism to provide a progeny which comprises, in the genome of one or more of its cells, both (i) one or more copies of the transposon and (ii) a gene encoding a transposase cognate for the transposon, wherein the gene encoding the transposase is under the control of one or more inducible regulatory sequences which permit expression of the transposase, and (d) expressing the gene encoding the transposase in the embryo, sperm or egg to cause mobilization of the transposon within a portion of the tissues or cells of the progeny. Using the method, mobilization of a transposon can advantageously be induced at predetermined stages of development of an embryo, sperm or egg and the mutated gene of a single cell may be replicated in subsequent cell divisions, resulting in groups of cells which are essentially homogenous for the transposed gene.

19 Claims, 22 Drawing Sheets

Figure 1: A self-inactivating autonomous transposon vector for inducible transposition Figure 3. Inducible exon trap system Figure 4. Inducible gene activation system A
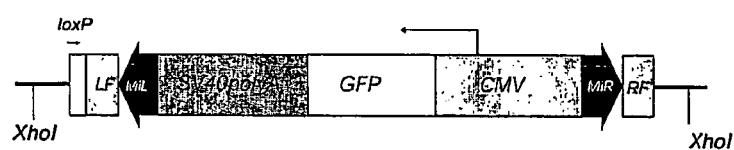
B
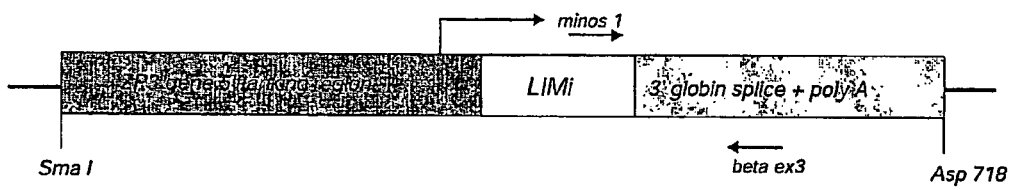
FIGURE 6

Figure 11
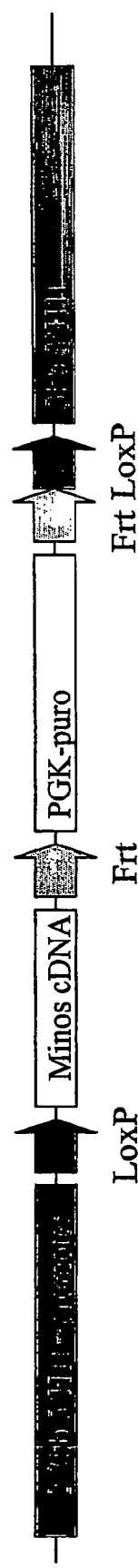
- Kozak sequence in constructs at the ATG
- *3' homology incudes TGA stem loop and Pu rich sequence
A
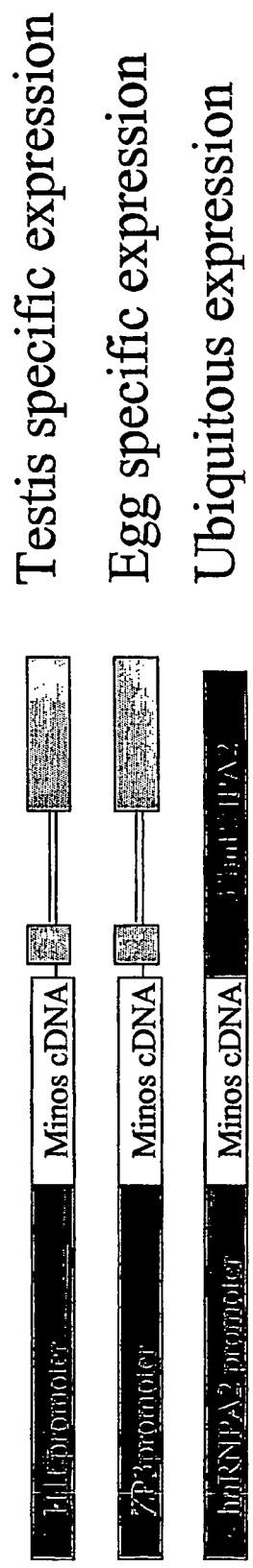
B Trap construct for transgenic mice and/or cloning into retroviral plasmid Dflank: small pieces of Drosophila DNA
RIR, LIR: Left and right inverted repeat sequence
TRE: Tet inducible CMV promoter
En2 SA: intron-splice acceptor
IRES/EGFP: internal ribosome binding site, flueorescent marker gene

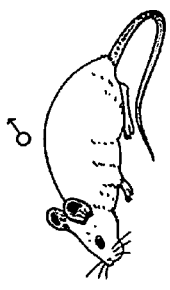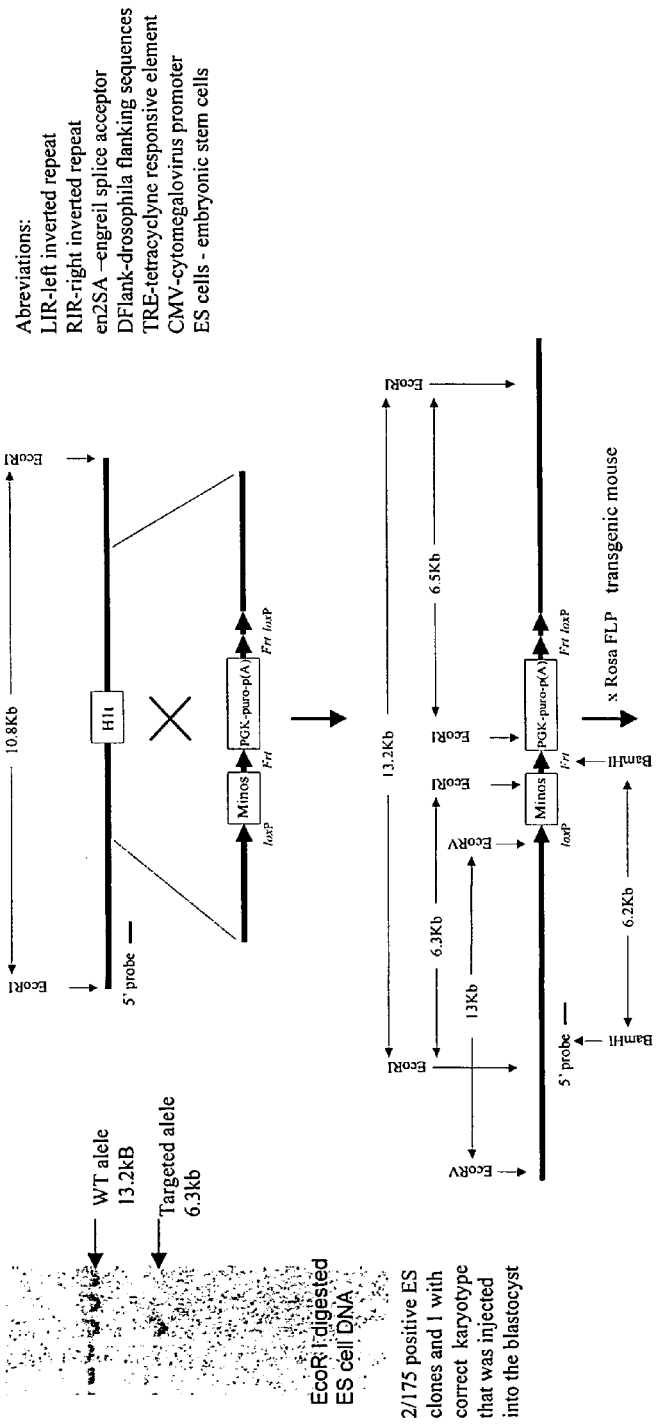
Fig. 16

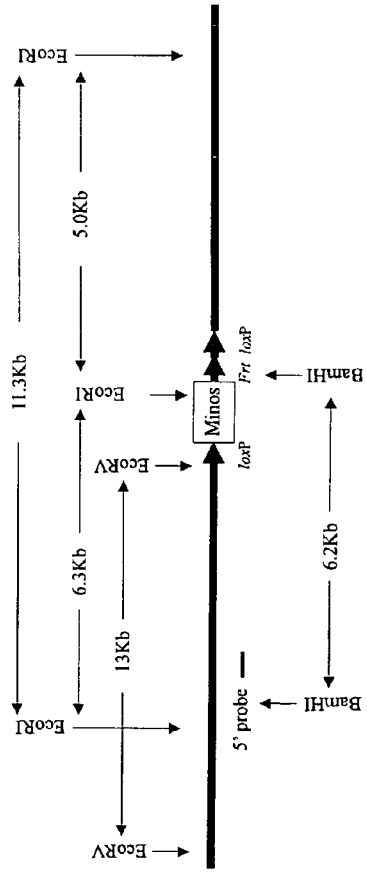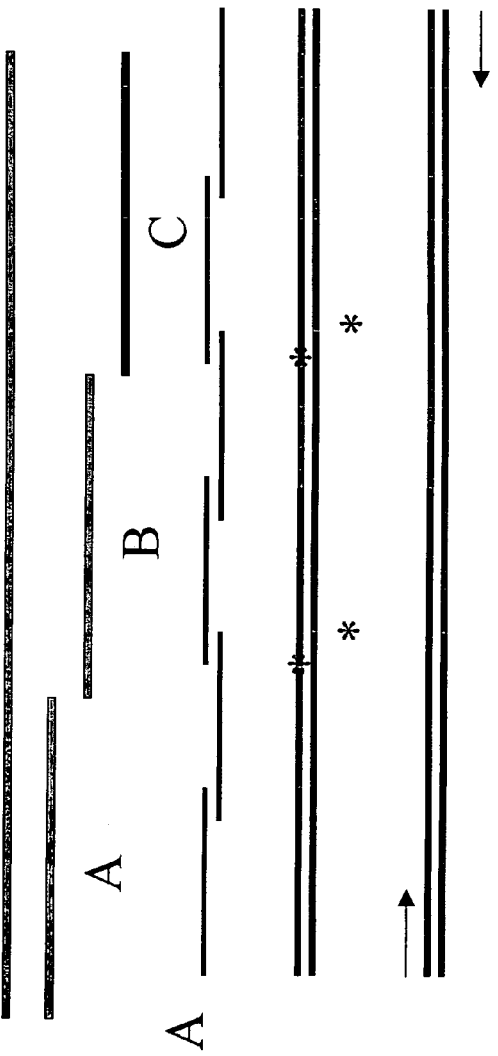
Fig. 17

Southern blot showing transposition events

Litters 04-12496 and 04-15687 came from breeding of non transgenic female with male 03-23830-07 (transgenic for Trap B and transposase)

Genomic DNA was digested with EcoRV (which does not cut in the Trap constructs) and probed with a 700 bp GFP fragment.

FISH on Trap-A jumps
Offspring
04-11761-01
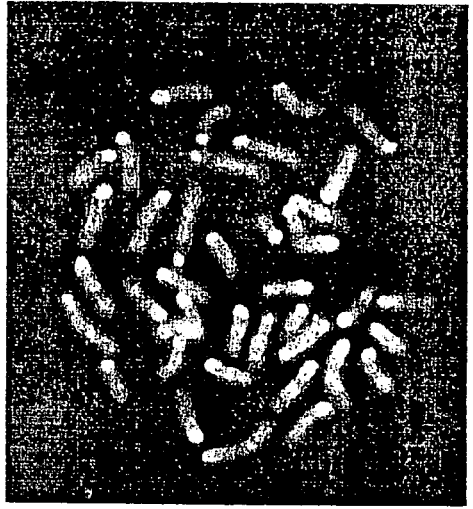
04-11761-02
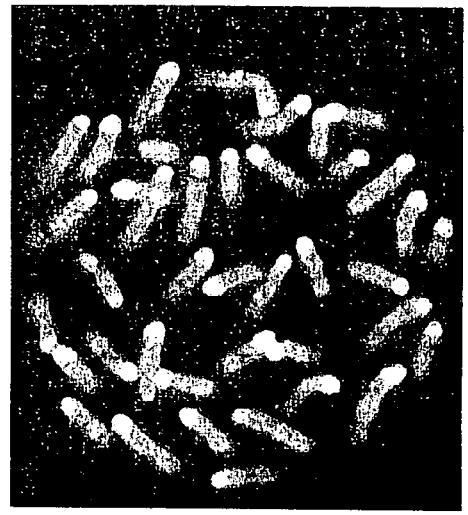
04-11761-03
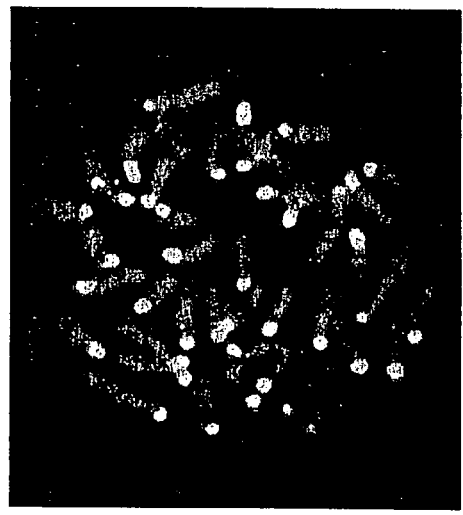
04-11761-04
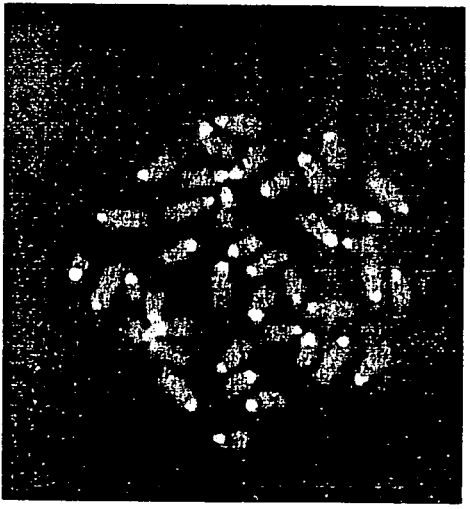
Parental line trap A (03-23712-05)
(initial integration on Chr.5)
Green: transposon probe landing
on different chromosomes after
Transposition as assayed on peripheral
blood cells
Fig 21

SEQUENCE LISTING

<160> NUMBER OF SEQ ID NOS: 28

<210> SEQ ID NO 1
<211> LENGTH: 34
<212> TYPE: DNA
<213> ORGANISM: Artificial
<220> FEATURE:
<223> OTHER INFORMATION: Synthetic Oligonucleotide Sequence

<400> SEQUENCE: 1
ataacttcgt atagcataca ttatacgaag ttat                                  34

<210> SEQ ID NO 2
<211> LENGTH: 21
<212> TYPE: DNA
<213> ORGANISM: Artificial
<220> FEATURE:
<223> OTHER INFORMATION: Synthetic Oligonucleotide Sequence

<400> SEQUENCE: 2
aagtgtaagt gcttgaaatg c                                                21

<210> SEQ ID NO 3
<211> LENGTH: 21
<212> TYPE: DNA
<213> ORGANISM: Artificial
<220> FEATURE:
<223> OTHER INFORMATION: Synthetic Oligonucleotide Sequence

<400> SEQUENCE: 3
gcatcaaatt gagttttgct c                                                21

<210> SEQ ID NO 4
<211> LENGTH: 1026
<212> TYPE: DNA
<213> ORGANISM: Drosophila hydei

<400> SEQUENCE: 4
atggtgcgcg gtaagcctat ctctaaggag atcagagtac tgatcaggga ctattttaag       60
tctgggaaga cactcactga gataagcaag cagttaaact tgcctaagag ctctgtgcat      120
ggggtgatac agattttcaa gaaaaatggg aacattgaga ataacatcgc gaatagaggc      180
cgaacatccg caataacccc ccgcgacaag agacagctgg ccaaaattgt gaaggctgac      240
cgccgccaat ccctgagaaa cttggcttcc aagtggtcgc agaccattgg caagactgtc      300
aagcgggagt ggacccggca gcaattaaag agtattggct acggttttta taaggccaag      360
gaaaaacccc tgcttacgct tcggcaaaaa agaagcgtc tgcaatgggc tcgggaaagg      420
atgtcttgga ctcaaaggca gtgggatacc atcatcttca gcgatgaggc taaatttgat      480
gtgagtgtcg gcgacacgag aaagcgcgtc atccgtaaga ggtccgagac ataccataag      540
gactgcctga aaagaacaac caagtttcct gcaagcacta tggtatgggg atgtatgtct      600
gccaaaggac tcgaaaagct tcacttcatc gaagggaccg ttaatgccga aaaatacatt      660
aacattctcc aggatagttt gctgccctca ataccaaaac tatccgattg tggtgaattc      720 actttttcagc aggacggagc atcatcgcac accgccaagc ggaccaaaaa ctggctgcag      780
tacaatcaga tggaggtgct cgattggccc tcaaatagtc cggatctaag cccaatcgaa      840
aatatctggt ggctaatgaa aaaccagctg cgaaacgagc cacagaggaa catttccgac      900
ttgaaaatca agctgcaaga gatgtgggac tcaatctctc aggagcactg caaaaacctg      960

```
ctcagcagca tgcctaaacg agtgaaatgc gtgatgcagg ccaagggcga cgttacacag    1020
ttctga                                                                1026

<210> SEQ ID NO 5
<211> LENGTH: 315
<212> TYPE: DNA
<213> ORGANISM: Artificial
<220> FEATURE:
<223> OTHER INFORMATION: Part A of Codon Optimized Transcript, Top
      strand

<400> SEQUENCE: 5
ccccgacgtc ccaccatggt gcgcggtaag cctatctcta aggagatcag agtactgatc      60
agggactatt ttaagtctgg aagacactc actgagataa gcaagcagtt aaacttgcct     120
aagagctctg tgcatggggt gatacagatt ttcaagaaaa atgggaacat tgagaataac     180
atcgcgaata gaggccgaac atccgcaata accccccgcg acaagagaca gctggccaaa     240
attgtgaagg ctgaccgccg ccaatccctg agaaacttgg cttccaagtg gtcgcagaca     300
attggcaaga ctgtc                                                     315

<210> SEQ ID NO 6
<211> LENGTH: 381
<212> TYPE: DNA
<213> ORGANISM: Artificial
<220> FEATURE:
<223> OTHER INFORMATION: Part B of Codon Optimized Transcript, Top
      Strand

<400> SEQUENCE: 6
ggggcaattg gcaagactgt caagcgggag tggacccggc agcaattaaa gagtattggc      60
tacggttttt ataaggccaa ggaaaaaccc ctgcttacgc ttcggcaaaa aaagaagcgt     120
ctgcaatggg ctcgggaaag gatgtcttgg actcaaaggc agtgggatac catcatcttc     180
agcgatgagg ctaaatttga tgtgagtgtc ggcgacacga aaaacgcgt catccgtaag      240 aggtccgaga cataccataa ggactgcctg aaaagaacaa ccaagtttcc tgcaagcact     300
atggtatggg gatgtatgtc tgccaaagga ctcggaaagc ttcacttcat cgaagggacc     360
gttaatgccg aaaaatacat t                                              381

<210> SEQ ID NO 7
<211> LENGTH: 421
<212> TYPE: DNA
<213> ORGANISM: Artificial
<220> FEATURE:
<223> OTHER INFORMATION: Part C of Codon Optimized Transcript, Top
      Strand

<400> SEQUENCE: 7
ccccaagctt cacttcatcg aagggaccgt taatgccgaa aaatacatta acattctcca      60
ggatagtttg ctgccctcaa taccaaaact atccgattgt ggtgaattca cttttcagca     120
ggacggagca tcatcgcaca ccgccaagcg gaccaaaaac tggctgcagt acaatcagat     180
ggaggtgctc gattggccct caaatagtcc ggatctaagc ccaatcgaaa atatctggtg     240
gctaatgaaa aaccagctgc gaaacgagcc acagaggaac atttccgact tgaaaatcaa     300
gctgcaagag atgtgggact caatctctca ggagcactgc aaaaacctgc tcagcagcat     360
gcctaaacga gtgaaatgcg tgatgcaggc caagggcgac gttacacagt tctgaggatc     420
c                                                                    421
```

```
<210> SEQ ID NO 8
<211> LENGTH: 19
<212> TYPE: DNA
<213> ORGANISM: Artificial
<220> FEATURE:
<223> OTHER INFORMATION: Synthetic Oligonucleotide

<400> SEQUENCE: 8
cagcttcgaa atgagccac                                              19

<210> SEQ ID NO 9
<211> LENGTH: 19
<212> TYPE: DNA
<213> ORGANISM: Artificial
<220> FEATURE:
<223> OTHER INFORMATION: Synthetic Oligonucleotide

<400> SEQUENCE: 9
tggacagcaa gaaagcgag                                              19

<210> SEQ ID NO 10
<211> LENGTH: 20
<212> TYPE: DNA
<213> ORGANISM: Artificial
<220> FEATURE:
<223> OTHER INFORMATION: Synthetic Oligonucleotide

<400> SEQUENCE: 10
cacaggacta gaacacctgc                                             20

<210> SEQ ID NO 11
<211> LENGTH: 19
<212> TYPE: DNA
<213> ORGANISM: Artificial
<220> FEATURE:
<223> OTHER INFORMATION: Synthetic Oligonucleotide

<400> SEQUENCE: 11
gctggtgaaa aggacctct                                              19

<210> SEQ ID NO 12
<211> LENGTH: 26
<212> TYPE: DNA
<213> ORGANISM: Artificial
<220> FEATURE:
<223> OTHER INFORMATION: Synthetic Oligonucleotide

<400> SEQUENCE: 12
aagagaataa aattctcttt gagacg                                      26

<210> SEQ ID NO 13
<211> LENGTH: 27
<212> TYPE: DNA
<213> ORGANISM: Artificial
<220> FEATURE:
<223> OTHER INFORMATION: Synthetic Oligonucleotide

<400> SEQUENCE: 13
gataatatag tgtgttaaac attgcgc                                     27

<210> SEQ ID NO 14
<211> LENGTH: 28
<212> TYPE: DNA
<213> ORGANISM: Artificial
<220> FEATURE:
```

```
<223> OTHER INFORMATION: Synthetic Oligonucleotide

<400> SEQUENCE: 14
caaaaatatg agtaatttat tcaaacgg                                          28

<210> SEQ ID NO 15
<211> LENGTH: 26
<212> TYPE: DNA
<213> ORGANISM: Artificial
<220> FEATURE:
<223> OTHER INFORMATION: Synthetic Oligonucleotide

<400> SEQUENCE: 15
gcttaagaga taagaaaaaa gtgacc                                            26

<210> SEQ ID NO 16
<211> LENGTH: 21
<212> TYPE: DNA
<213> ORGANISM: Artificial
<220> FEATURE:
<223> OTHER INFORMATION: Transposon Flanking Sequence

<400> SEQUENCE: 16
gcacgttagc agcttctacg a                                                 21

<210> SEQ ID NO 17
<211> LENGTH: 21
<212> TYPE: DNA
<213> ORGANISM: Artificial
<220> FEATURE:
<223> OTHER INFORMATION: Transposon Flanking Sequence

<400> SEQUENCE: 17
atagctatag tggtaatacg a                                                 21

<210> SEQ ID NO 18
<211> LENGTH: 21
<212> TYPE: DNA
<213> ORGANISM: Artificial
<220> FEATURE:
<223> OTHER INFORMATION: Transposon Flanking Sequence

<400> SEQUENCE: 18
atttttctta cctacatacg a                                                 21

<210> SEQ ID NO 19
<211> LENGTH: 21
<212> TYPE: DNA
<213> ORGANISM: Artificial
<220> FEATURE:
<223> OTHER INFORMATION: Transposon Flanking Sequence

<400> SEQUENCE: 19
acacacaaaa taacattacg a                                                 21

<210> SEQ ID NO 20
<211> LENGTH: 21
<212> TYPE: DNA
<213> ORGANISM: Artificial
<220> FEATURE:
<223> OTHER INFORMATION: Transposon Flanking Sequence

<400> SEQUENCE: 20
ttagacagct caatgttacg a                                                 21
```

```
<210> SEQ ID NO 21
<211> LENGTH: 21
<212> TYPE: DNA
<213> ORGANISM: Artificial
<220> FEATURE:
<223> OTHER INFORMATION: Transposon Flanking Sequence

<400> SEQUENCE: 21
tcgtagaaaa cgaaaaatat c                                              21

<210> SEQ ID NO 22
<211> LENGTH: 21
<212> TYPE: DNA
<213> ORGANISM: Artificial
<220> FEATURE:
<223> OTHER INFORMATION: Transposon Flanking Sequence

<400> SEQUENCE: 22
tcgtagaggt atgattccta t                                              21

<210> SEQ ID NO 23
<211> LENGTH: 21
<212> TYPE: DNA
<213> ORGANISM: Artificial
<220> FEATURE:
<223> OTHER INFORMATION: Transposon Flanking Sequence

<400> SEQUENCE: 23
tcgtacatgt gcatatatgg c                                              21

<210> SEQ ID NO 24
<211> LENGTH: 23
<212> TYPE: DNA
<213> ORGANISM: Artificial
<220> FEATURE:
<223> OTHER INFORMATION: Transposon Flanking Sequence

<400> SEQUENCE: 24
tcgtattctc atcttcttaa tat                                            23

<210> SEQ ID NO 25
<211> LENGTH: 21
<212> TYPE: DNA
<213> ORGANISM: Artificial
<220> FEATURE:
<223> OTHER INFORMATION: Transposon Flanking Sequence

<400> SEQUENCE: 25
tcgtatcatt catgatgcat t                                              21

<210> SEQ ID NO 26
<211> LENGTH: 300
<212> TYPE: DNA
<213> ORGANISM: Artificial
<220> FEATURE:
<223> OTHER INFORMATION: Part A of Codon Optimized Transcript, Bottom
      Strand

<400> SEQUENCE: 26
ggggactagt ccaattgtct gcgaccactt ggaagccaag tttctcaggg attggcggcg     60
gtcagccttc acaattttgg ccagctgtct cttgtcgcgg ggggttattg cggatgttcg    120
gcctctattc gcgatgttat tctcaatgtt cccattttc ttgaaaatct gtatcacccc    180
atgcacagag ctcttaggca agtttaactg cttgcttatc tcagtgagtg tcttcccaga    240
cttaaaatag tccctgatca gtactctgat ctccttagag ataggcttac cgcgcaccat    300
```

<210> SEQ ID NO 27
<211> LENGTH: 395
<212> TYPE: DNA
<213> ORGANISM: Artificial
<220> FEATURE:
<223> OTHER INFORMATION: Part B of Codon Optimized Transcript, Bottom
      Strand

<400> SEQUENCE: 27
ccccatgcat ccccaagctt tccgagtcct ttggcagaca tacatcccca taccatagtg      60
cttgcaggaa acttggttgt tcttttcagg cagtccttat ggtatgtctc ggacctctta     120
cggatgacgc gttttctcgt gtcgccgaca ctcacatcaa atttagcctc atcgctgaag     180
atgatggtat cccactgcct ttgagtccaa gacatccttt cccgagccca ttgcagacgc     240
ttcttttttt gccgaagcgt aagcaggggt ttttccttgg ccttataaaa accgtagcca     300
atactcttta attgctgccg ggtccactcc cgcttgacag tcttgccaat tgtctgcgac     360
cacttggaag ccaagtttct cagggattgg cggcg                                395

<210> SEQ ID NO 28
<211> LENGTH: 405
<212> TYPE: DNA
<213> ORGANISM: Artificial
<220> FEATURE:
<223> OTHER INFORMATION: Part C of Codon Optimized Transcript, Bottom
      Strand

<400> SEQUENCE: 28
ctgtgtaacg tcgcccttgg cctgcatcac gcatttcact cgtttaggca tgctgctgag      60 caggttttttg cagtgctcct gagagattga gtcccacatc tcttgcagct tgattttcaa    120
gtcggaaatg ttcctctgtg gctcgtttcg cagctggttt ttcattagcc accagatatt     180
ttcgattggg cttagatccg gactatttga gggccaatcg agcacctcca tctgattgta     240
ctgcagccag tttttggtcc gcttggcggt gtgcgatgat gctccgtcct gctgaaaagt     300
gaattcacca caatcggata gttttggtat tgagggcagc aaactatcct ggagaatgtt     360
aatgtatttt tcggcattaa cggtcccttc gatgaagtga agctt                     405

TRANSGENIC MICE GENERATED BY TRANSPOSITION AND USES THEREOF

RELATED APPLICATIONS

This application is a continuation-in-part which claims priority under 35 U.S.C. §120 to PCT Application Serial PCT/GB03/00065, filed Jan. 9, 2003, which claims priority under 35 U.S.C. §119 to U.S. Provisional Application 60/347,107, filed Jan. 9, 2002, Great Britain Application Serial No. 0200419.0, filed Jan. 9, 2002, and Great Britain Application Serial No. 0211242.3, filed May 16, 2002, the entireties of which are incorporated herein by reference.

FIELD OF THE INVENTION

The present invention relates to a method for the transfer of genetic information in an organism using transposons. In particular, it relates to a method of inducing genetic modification of cells at a predetermined stage of development.

BACKGROUND TO THE INVENTION

The development of high through-put DNA sequencing technology, and sophisticated data-capture and computational analysis has resulted in the sequence determination of entire genomes including *Drosophila melanogaster* and *Homo sapiens*. This has identified novel "predicted" gene sequences but no associated biology ascribing function. Functional information is a prerequisite to delineate which genes may prove to be therapeutic targets for disease management and diagnosis in man.

The identification of individual gene function and the functional relationship of genes to disease states is now a preoccupation of the Biotechnology and Pharmaceutical industry. The identification of disease related genes will allow the development of new drugs or targets for drug discovery, provide diagnostic or prognostic markers for disease and provide prescriptive guides for physicians. The latter of these will be particularly useful in diseases having complex genetics. Where genetic variation between patients can be measured, personalised medicine programs can be developed where defined patient responses to drug action are identified. The approach is expensive and time consuming, and the outcomes often subjective, lacking hard evidence relating a variation in gene expression to a functional disease related event in vivo. Validation of gene function requires studies in animal model systems which directly relate cause (i.e. a mutation in a gene sequence, a deletion or an insertion) with a measurable effect (i.e. behavioural, developmental, metabolic etc.) in the whole animal.

Gene function studies in mice and other mammals are presently restricted to:

A) Painstaking mutational analysis of individual genes in "knock-out" mice derived from libraries of embryonic stems cells (ES cells) each cell containing one or more tagged genes often introduced by viral infection.

B) The random mutation in vivo of mouse genes by alkylating agents, and subsequently whole genome sequence analysis to identify multiple mutations.

The knockout approach is valid where a function can be surmised based on sequence homology with closely related genes of known function but this approach is time consuming and labour intensive.

The alkylation approach relies entirely on whole genome sequencing to identify sites of mutation and the cataloguing of changes in previously determined behavioural traits and metabolic read-outs. Identification of a phenotypic change must then be correlated to one of perhaps one hundred alkylation events in the target mouse genome. The approach is also time consuming and requires the generation and maintenance of large mouse libraries, and is limited to inbred strains of mice (for comparative review see Abuin et al. (2002) *TIB* 20:36-42).

Another method for obtaining mutations is through the introduction of exogenous DNA into the genome.

Transposons are natural genetic elements capable of jumping or transposing from one position to another within the genome of a species. Mobilisation of a transposon is dependant on the expression of a transposase enzyme which binds to sequences flanking the transposon DNA leading to the excision of DNA from one position in the genome and reinsertion elsewhere in the genome. Insertion into a gene sequence will lead to a change in gene function which may, in turn, result in a measurable phenotypic change in the whole organism.

Of the three "classical" model animals, the fly, the worm and the mouse, efficient transposon based insertion methodologies have been developed for *D. melanogaster* and for *C. elegans*. The following class 2 transposon families have been identified: 1) the P family; 2) the hAt family (hobo-Ac-Tam3), (including for example hermes) and the Tcl/mariner family (including for example minos, mariner and sleeping beauty).

The introduction of P element mediated transgenesis and insertional mutagenesis in *Drosophila* (Spradling & Rubin (1982) *Science* 218:341-347) transformed *Drosophila* genetics and formed the paradigm for developing equivalent methodologies in other eukaryotes. However, the P element has a very restricted host range, and therefore other elements have been employed in the past decade as vectors for gene transfer and/or mutagenesis in a variety of complex eukaryotes, including nematodes, plants, mammals, fish e.g. zebrafish and birds.

The use of *Drosophila* P-elements in *D. melanogaster* for enhancer trapping and gene tagging has been described; see Wilson et al. (1989) *Genes Dev* 3:1301; Spradling et al. (1999) *Genetics* 153:135.

The hobo element of *Drosophila melanogaster* has been described by Gelbart W. M., Blackman R. K., (1989) *Prog Nucleic Acid Res Mol Biol* 36:37-46.

Hermes is derived from the common housefly. Its use in creating transgenic insects is described in U.S. Pat. No. 5,614,398, incorporated herein by reference in its entirety.

Minos, a class 2 transposon and member of the Tcl family of elements, was isolated from *D. hydei* and has been used for the germ line transformation of *D. melanogaster, C. capitata*, and *Anopheles stephensi* (Loukeris, T. G. et al. (1995) *Proc Natl Acad Sci USA* 92:9485-9; Loukeris, T. G. et al. (1995) *Science* 270:2002-5, Catteruccia, F. et al. (2000) *Nature* 405: 959-962) and using transient mobilisation assays it has also been shown to be active in embryos of *D. melanogaster, Aedes aegypti, Anopheles stephensi* and *Bombyx mori* and in cell lines of *D. melanogaster, Aedes aegypti, Anopheles gambiae* and *Spodoptera frugiperda* (Catteruccia, F. et al. (2000) *Proc Natl Acad Sci USA* 97:2157-2162, Klinakis et al. (2000) *EMBO Reports* 1:416-421; Shimizu et al. (June 2000) *Insect Mol Biol* 9(3):277-81).

European Patent Application 0955364 (Savakis et al., the disclosure of which is incorporated herein by reference) describes the use of Minos to transform cells, plants and animals. The generation of transgenic mice comprising one or more Minos insertions is also described.

Mariner is a transposon originally isolated from *Drosophila mauritiana*, but since discovered in several invertebrate and vertebrate species. The use of mariner to transform organisms is described in International patent application WO99/09817.

Salmonid type transposons such as the Sleeping Beauty (SB) transposon, a Tc1/mariner-like transposable element reconstructed from fish have been described by Ivics et al. (1997) *Cell* 91:501-510 and Horie et al. (2001) *Proc Natl Acad Sci USA* 98, Issue 16, 9191-9196.

International Patent Application WO99/07871 describes the use of the Tc1 transposon from *C. elegans* for the transformation of *C. elegans* and a human cell line.

PiggyBac is a transposon derived from the baculovirus host *Trichplusia ni*. Its use for germ-line transformation of Medfly has been described by Handler et al. (1998) *PNAS (USA)* 95:7520-5 and U.S. Pat. No. 6,218,185.

In the techniques described in the prior art, the use of the cognate transposase for inducing transposon jumping (or transposition) is acknowledged to be necessary.

The standard methodology for transposable element mediated transformation is by coinjecting into pre-blastoderm embryos a mixture of two plasmids: one expressing transposase (Helper) but unable to transpose, and one carrying the gene of interest flanked by the inverted terminal repeats of the element (Donor). Transformed progeny of injected animals are detected by the expression of dominant marker genes.

PCT/EP01/03341 (WO 01/71019) describes the generation of transgenic animals using transposable elements. According to this method, the transposase function is provided by crossing of transgenic organisms, one of which provides a transposon function and the other providing a transposase function in order to produce organisms containing both transposon and transposase in the required cells or tissues. The use of tissue specific chromatin opening domains directs transposase activity in a tissue specific manner and gives rise to multiple independent transposition events in somatic tissues (see Zagoraiou et al. (2001) *PNAS* 98:11474-11478).

Transpositions can be "tagged" allowing positional changes within complex genomes to be rapidly determined and flanking genes determined by sequence analysis. This allows an immediate link between cause (i.e. an insertional event in a specific gene or regulatory element) and effect (i.e. a phenotypic or measurable change). However, conventional methods of inducing genetic modifications by transposition suffer from the disadvantage that the tissue in which transposition has occurred will be a mosaic of individual cells each with unique transpositions. As a result, analysis of phenotype results of the transposition event may be difficult to perform as each transposition event is unique. Thus, a method of controlling a transposition event so as to provide the same genetic modification in a number of cells would provide a valuable contribution to the art.

SUMMARY OF THE INVENTION

According to a first aspect of the present invention, there is provided a method of generating a transgenic progeny and inducing transposition, comprising the steps of:

(a) generating a first adult transgenic organism comprising within its genome one or more copies of a transposon;

(b) generating a second adult transgenic organism comprising within its genome one or more copies of a gene encoding a transposase cognate for the transposon and/or an element capable of regulating expression of the gene encoding the transposase;

(c) crossing the first adult transgenic organism with the second transgenic adult organism to provide a progeny which comprises, in the genome of one or more of its cells, both (i) one or more copies of the transposon and (ii) a gene encoding a transposase cognate for the transposon, wherein the gene encoding the transposase is under the control of one or more regulatory sequences which permit expression of the transposase; and (d) expressing the gene encoding the transposase in the progeny to cause mobilisation of the transposon within a portion of the tissues or cells of the progeny.

In one embodiment the gene encoding the transposase is under the control of an inducible promoter.

Alternatively expressed, the invention thus provides a method of generating a transgenic progeny by transposon mobilisation, comprising the steps of:

(a) providing a progeny which comprises, in the genome of one or more of its cells, both (i) one or more copies of a transposon and (ii) one or more genes encoding a transposase cognate for the transposon, wherein the gene encoding the transposase is under the control of one or more regulatory sequences which permit expression of the transposase, and (b) expressing the transposase in the progeny to cause mobilisation of the transposon within a portion of the tissues or cells of the progeny.

Suitably, the first adult transgenic organism can be transgenic lines comprising stably integrated "dormant" transposons. Such transgenic lines can be generated using standard genetic modification technologies. Dormant transposons can be induced to transpose through crossing with the second adult transgenic organism. Accordingly, the invention provides a method which can allow the rapid generation of thousands of mutant progeny, such as mouse mutants.

By "progeny" is meant a double positive transgenic organism that comprises in the genome of one or more of its cells both 1) one or more copies of a transposon and 2) one or more copies of a gene encoding a transposase. A "progeny" as used herein, can be obtained by methods well known in the art including, but not limited to 1) co-injection of a transposon and a transposase gene into the fertilized eggs of an organism; 2) crossing of an organism comprising one or more copies of a transposon with a second organism comprising one or more copies of a gene encoding a transposase; 3) injecting a transposase gene into the eggs of an organism comprising one ore more copies of a transposon; and 4) injecting a transposon into an organism comprising one or more copies of a gene encoding a transposase.

A "progeny" according to the invention is also made by using ES cells, for example, ES cells that are transfected or infected with one or more of a transposon and a transposase gene, wherein the ES cells are placed back into an early embryo to obtain the desired modification. Alternatively, a combination of ES technology and egg injection technology is used to obtain a "progeny" of the invention.

In a preferred embodiment, the one or more regulatory sequences which permit expression of the transposase are sequences which allow specific expression of the transposase during germline development. Accordingly, the germ cells of the progeny have transposition events.

FIG. 13 is a schematic diagram showing in vivo transposition in the egg or early embryo. Double positive female progeny are obtained after crossing. In one embodiment, a double positive female progeny is produced by crossing a transposon-positive male and a transposase-positive female, as depicted in FIG. 13. Alternatively, a double positive male progeny is produced by crossing a transposon-positive female and a transposase-positive male.

Accordingly, in one embodiment, the progeny is a female transgenic organism resulting from reproduction between the first and second transgenic organisms referred to above. In this embodiment, the one or more regulatory sequences which permit expression of the transposase are sequences which allow specific expression of the transposase during oogenesis in the female progeny. Thus, transposase expression is induced upon oogenesis. This, in turn leads to germline transposition events taking place in oocytes to generate oocytes having inserted sequences.

In this embodiment, the one or more regulatory sequences which permit expression of the transposase are derived from regulatory sequences for genes which are expressed in developing oocytes. Suitable regulatory sequences include those which control the expression of oocytes genes such as Zp3, Zp1, Zp2, Gdf9, Bmp15, Figla and Mater (see, for example, Rajkovic & Matzuk (2002) *Molecular and Cellular Endocrinology* 187:5-9). Other suitable regulatory sequences may be derived from the regulatory sequences of Oct-4.

FIG. 14 is a schematic diagram showing in vivo transposition in the sperm. In one embodiment, a double positive male progeny is produced by crossing a transposon-positive female and a transposase-positive male, as depicted in FIG. 14. Alternatively, a double positive male progeny is produced by crossing a transposon-positive male and a transposase-positive female.

In one embodiment, in vivo transposition occurs wherein the male contributes both the transposon and the transposase. Transposition takes place in the sperm. Mutants are obtained after crossing to a female.

Accordingly, in another embodiment, the progeny is a male transgenic organism resulting from reproduction between the first and second transgenic organisms referred to above. In this embodiment, the one or more regulatory sequences which permit expression of the transposase are sequences which allow specific expression of the transposase during spermatogenesis in the male progeny. Thus, transposase expression is induced upon spermatogenesis. This, in turn leads to germline transposition events taking place in spermatocytes to generate spermatocytes having inserted sequences.

In this embodiment, the one or more regulatory sequences which permit expression of the transposase are derived from regulatory sequences for genes which are expressed in developing spermatocytes. Suitable regulatory sequences include those which control the expression of spermatocyte specific mRNAs such as the transcript of the H1t gene (Bartell et al. (August 2000) *Biol Of Reproduction* 63(2):409-16).

Suitably, the progeny which have transposition events taking place in the germline are then mated to produce offspring in which the transposition events can be characterised. A progeny having germline transposition can be mated to a normal organism or to an organism which, itself has been generated to have germline transposition. In one embodiment, the transposase gene comprises a site that allows for elimination of the transposase gene by excision. For example, the invention provides for a transposon-positive/transposase gene positive organism (either male or female), wherein the transposase gene comprises a 10× or FRT site and can be excised by cre or FLP, respectively. In one embodiment, a male double positive organism is mated to a female organism, wherein the female comprises cre or flp recombinaase in the egg, thereby removing the transposase gene from the early embryo. In another embodiment, a male double positive organism is mated to a normal female (that is a female that does not comprise cre or flp recombinase). The offspring that results from this mating may not have stable transpositions. The above described matings are also performed with a female double positive organism mated with a male.

In a further embodiment the invention, the "progeny" is an embryo. Accordingly, in this embodiment, there is provided a method of generating a transgenic embryo and inducing transposition, comprising the steps of:

a) generating a first adult transgenic organism comprising within its genome one or more copies of a transposon;

b) generating a second adult transgenic organism comprising within its genome one or more copies of a gene encoding a transposase cognate for the transposon and/or an element capable of regulating expression of the gene encoding the transposase;

c) crossing the first adult transgenic organism with the second transgenic adult organism to provide an embryo which comprises, in the genome of one or more of its cells, both (i) one or more copies of the transposon and (ii) a gene encoding a transposase cognate for the transposon, wherein the gene encoding the transposase is under the control of one or more regulatory sequences which permit expression of the transposase; and d) expressing the gene encoding the transposase in the embryo to cause mobilisation of the transposon within a portion of the tissues or cells of the embryo.

Alternatively expressed, the invention thus provides a method of generating a transgenic embryo by transposon mobilisation, comprising the steps of:

a) providing an embryo which comprises, in the genome of one or more of its cells, both (i) one or more copies of a transposon and (ii) one or more genes encoding a transposase cognate for the transposon, wherein the gene encoding the transposase is under the control of one or more regulatory sequences which permit expression of the transposase, and b) expressing the transposase in the embryo to cause mobilisation of the transposon within a portion of the tissues or cells of the embryo.

"Embryo" as herein described should be understood to refer to the structure developing from a single fertilised egg or zygote to the time of birth or hatching in the case of vertebrates or invertebrates or germination in the case of plants. Thus, in the context of the present invention, "embryo" should be understood to also encompass a mammalian fetus.

FIG. 15 is a schematic diagram showing in vivo transposition using ubiquitous expression. According to this embodiment, either of the male or female contributes the transposon, and either of the male or female contributes the transposase. Transposition takes place in the egg, early embryo or sperm.

Mobilisation of a transposon in embryonic cells or tissues may be induced at any time during the development of the embryo, for example at predetermined stages of development of an embryo. By inducing transposition during such stages of development, the mutated gene of a single cell may be replicated in subsequent cell divisions, resulting in a group or groups of cells which are essentially homogeneous for the transposed gene, only if the transposase is no longer active (for example, if the transposase gene has been excised as described herein). Thus the transposed gene may be present in some or all of the cells of a particular tissue or group of tissues. The invention thus enables the generation of transgenic embryos and organisms comprising one or more clonal populations of cells homogeneous for one or more individual mutations.

Thus, a second aspect of the invention provides a method of generating a transgenic organism having a plurality of cells or tissues homogeneous for a gene modified by transposon mobilisation, the method comprising generating a transgenic embryo and inducing transposition therein according to the method of the first aspect of the invention.

By enabling the regulation of transposition at different times during development, the method of the present invention also increases the likelihood of genome-wide transposition since chromatin domains accessible to transcriptional complexes and, in all probability, transposition events vary in different cell tissue types at different times during embryonic development and moreover in adult life and in abnormal growth situations such as tumours.

The likelihood of achieving transposition in particular regions of the genome may be increased further by the use of chromatin opening domains, for example ubiquitously-acting chromatin opening elements (UCOEs) (PCT/GB99/02357 (WO 0005393)), locus control regions (LCRs) (Fraser, P. & Grosveld, F. (1998) *Curr Opin Cell Biol* 10:361-365), CpG islands or insulators to control expression of the transposon and/or the gene encoding the transposase.

In preferred embodiments of the invention, the transposon and/or the gene encoding the transposase and/or a sequence regulating expression of the gene encoding the transposase are incorporated within chromatin opening domains to increase the likelihood of achieving transposition in a target tissue of the embryo, thus enabling the generation of a population of cells of that tissue homogeneous for a transposition event. For example, where it is desired to induce transposition in a defined tissue, the transposon and/or gene encoding the transposase and/or a sequence regulating expression of the gene encoding the transposase are incorporated within a locus control region, conferring tissue specific control on the expression of a transgene in that tissue. Where it is desired to induce transposition in a tissue for which specific LCRs are not available and/or where it is desired to induce early induction of transposition in a particular tissue, the transposon and/or the gene encoding the transposase and/or a sequence regulating expression of the gene encoding the transposase may be incorporated within a UCOE. In particularly preferred embodiments of the invention, both the transposon and the gene encoding the transposase are incorporated within chromatin opening domains. This advantageously enhances the efficiency of transposition in particular loci throughout the genome during embryo development, enabling the production of one or more populations of cells homogeneous for a particular transposition event.

Thus the invention further provides in a third aspect a method of generating a transgenic embryo and inducing transposition, comprising the steps of:
  (a) generating a first adult transgenic organism comprising within its genome one or more copies of a transposon;
  (b) generating a second adult transgenic organism comprising within its genome one or more copies of a gene encoding a transposase cognate for the transposon and/or an element capable of regulating expression of the gene encoding the transposase;
  (c) crossing the first adult transgenic organism with the second transgenic adult organism to provide an embryo which comprises, in the genome of one or more of its cells, both (i) one or more copies of the transposon and (ii) a gene encoding a transposase cognate for the transposon, wherein the gene encoding the transposase is under the control of one or more regulatory sequences which permit expression of the transposase and wherein the transposon and/or the gene encoding the transposase and/or a gene regulating expression of the gene encoding the transposase lie within a chromatin opening domain; and
  (d) expressing the gene encoding the transposase in the embryo to cause mobilisation of the transposon within a portion of the tissues or cells of the embryo.

In preferred embodiments of the invention, the embryo is produced by crossing a first organism, which is a transgenic organism comprising one or more copies of the transposon, with a second organism, which is a transgenic organism which comprises, in its genome one or more copies of the regulatable gene encoding a cognate transposase. In an alternative embodiment, the embryo may be produced by crossing a first organism, which is a transgenic organism comprising one or more copies of both the transposon and the gene encoding the cognate transposase with a second organism comprising one or more copies of regulatory elements necessary to permit transposase expression.

In a preferred embodiment, the transposon and the gene encoding the transposase may be provided as a single construct such that the gene encoding the transposase is disrupted when the transposon mobilises, thus limiting further mobilisation of the transposon. This may be achieved by placing one of the inverted repeats of the transposon in an intron which interrupts the transposase gene such that the transposase gene is disrupted when the transposon is mobilised. This vector enables a single cross step to be used to generate a transgenic organism that contains regulator, transposase gene and transposon. Further, transposition leads to complete inactivation of the transposase source, resulting in stability of the new insertion even in the presence of inducer. FIG. 1 illustrates schematically the use of such a vector in the present invention.

The incorporation of Cre/lox functions (details of which are reviewed in Sauer (1993) *Methods of Enzymology* 225: 90-900) or Flp/frt functions (Farley et al. (2000) *Genesis* 28:106-110; Schaft et al. (2001) *Genesis* 31:6-10) and different transposon/transposase combinations may also be used to eliminate primary transposase function. In further embodiments of the invention, however, the transposase gene is not destroyed on transposition, thus allowing further transposon mobilisation on, for example, administration of inducer.

In methods of the invention, transposition may be induced using any system known to the skilled person. Transposition may be induced by induction of transposase gene expression via application of an endogenous substance or via operation of an endogenous signal, such as a developmental regulated signal.

The one or more regulatory sequences of which the gene encoding the transposase is under the control may be inducible regulatory sequences. For example, suitable induction systems include tet based systems, the lac operator-repressor system, ecdysone based systems and oestrogen based systems, details of which are provided infra. Exogenous inducers may be provided in any convenient fashion, e.g. by injection to the maternal animal or embryo or as an additive to the food or water supply to the maternal animal. Transposition may be induced at one or more times during embryo development. Thus inducers may be administered only once or repeatedly during one or more stages of development.

In alternative embodiments of the invention, expression of the gene encoding the transposase may be induced in response to a gene regulatory signal produced at a particular stage of embryo development. Such control may be achieved by placing the gene encoding the transposase under the control of a gene regulatory sequence such as a developmental regulated sequence or promoter, for example, a developmental regulated specific promoter responsive to a particular gene regulatory signal such as a transiently expressed development regulated protein. Where the gene encoding the transposase is under such control, expression of the gene encoding the transposase will only occur when the gene regulatory signal, for example a transiently expressed developmental regulated protein, is produced, or, alternatively, when such a signal protein is introduced to the embryo, for example by injection or in the feed of the maternal animal.

Using the methods of the invention, the timing of the expression of the gene encoding the transposase and hence the timing of the induction of transposition in an embryo may be controlled.

In embodiments where it is desired to tightly control the duration and effect of expression of the transposase gene and thus further restrict the timing of transposition, the gene encoding the transposase may be provided within the same construct as the transposon such that, on transposon mobilisation, the gene encoding the transposase is disrupted, preventing the production of further transposase and thus limiting further transposition.

By thus selecting the time of induction, mobilisation of transposons may be induced at a predetermined stage of embryo development. For example, transposition may be induced at very early stages of development such as at the zygote stage, a four cell embryo, sixty-four cell embryo etc. or at later stages of development.

In one embodiment, induction of transposition by placing the transposase under the control of one or more regulatory sequences that will drive transposase gene expression in the early fertilised egg e.g. at the two or four cell stage is desirable. Suitable regulatory sequences for controlling transposase expression at this stage may be derived from the regulatory sequences of genes whose expression is activated at this stage. Such genes include Oct-4 (Kirchof et al. (December 2000) *Biol Reprod* 63(6):1698-705), and maternal effect genes such as Zp1, Zp2, Gdf9, Bmp15, Figla and Mater. Other suitable genes include hsp70.1 (Bevilacqua et al. (April 2000) *Development* 127(7):1541-51).

In another embodiment, induction of transposition by placing the transposase under the control of one or more regulatory sequences that will drive transposase gene expression in the early sperm is desirable. Suitable regulatory sequences for controlling transposase expression at this stage may be derived from the regulatory sequences of genes whose expression is activated at this stage. Such genes include the early histone sperm specific promoter (for example the H1t promoter (see Wolfe et al., 2003, *Biology of Reproduction*, 68:2267-2273)). In one embodiment of the invention a transposase is integrated into the endogenous H1t locus. The invention therefore encompasses all of the regulatory sequences present in the endogenous H1t locus. The invention also contemplates any regulatory sequence that will drive transposase expression in the sperm that is known in the art.

Depending on the stage of development, cells in which transposition has occurred may divide with further rounds of cell divisions resulting in a population of cells homogeneous for the initial transposition event. Where transposition has been induced more than once, a population of cells may be homogeneous for each of two or more transposition events. Thus, depending on the stage of development, an insertional event may be present in populations of cells within one or more tissues, complete tissues or groups of tissues. The precise nature of the insertional event will determine whether it will influence functional gene expression in some or all embryonic and adult tissues. Thus, gene expression patterns of modified genes can be monitored during embryo development and in adult cells and tissues.

Moreover, similar populations of cells homogeneous for an initial transposition event can also be generated in rapidly growing adult cells and tissue derived from stem cells, typically during tissue regeneration or during cell and tissue maintenance. Examples of such cells and tissues include but are not limited to cells of the gut lining, the liver and blood, which are subject to rapid turnover and/or regeneration from stem cells in the adult. Similarly, populations of cells homogeneous for a transposition event may be generated in tumours. The methods of the invention may be adapted to provide populations of cells homogeneous for an initial transposition event in such adult cells.

Thus, in further embodiments of the invention, step (d) of the first or third aspect of the invention may be adapted by expressing the gene encoding the transposase in a neonatal, young adult or adult organism to cause mobilisation of the transposon within a portion of the tissues or cells of the organism instead of or, preferably, in addition to expressing the transposase in the embryo. Thus, the method of the invention enables the generation of a population of cells homogeneous for a transposition event induced at a predetermined stage of development in a neonate, young adult or adult organism. In such embodiments, the transposon or the gene encoding the transposase is preferably under the control of a locus control region to enable tissue specific control of the transgene. For example, where it is desired to induce transposition in liver cells, the gene encoding the transposase may be under the control of a locus control region associated with expression in liver cells.

Where transposition events are induced in the early development of the zygote, it is possible to develop ES cell lines having transpositions. These ES cell lines can be sequenced, characterised and stored for future use.

The generation of genetic mutations in transgenic organisms as a result of transposon insertion according to the invention may give rise to novel phenotypic variations in the organisms. Using the methods of the invention, transgenic embryos may be produced in which one or more clusters of cells or tissues are each homogeneous for a different transposition event, each of which may or may not have a phenotypic effect. Thus using the methods of the invention, embryos and adults developed therefrom comprising one or more clusters or groups of cells each displaying a phenotypic variation compared to the phenotype of corresponding cells or tissues in which no insertional event has occurred may be produced.

The effect of a transposition event on the phenotype of the transgenic embryo will, of course, depend to some extent on the developmental stage at which transposition occurs. Where transposition is induced, for example at the single zygote stage, all cells of the embryo developed therefrom will be homogeneous for the insertional event. Thus, if the transposition event, e.g. insertional event, results in change in phenotype which is lethal to each cell, the embryo will not develop. Where the transposition event(s) has been induced at a later stage of development, each insertional event will be present in the cluster of cells or tissues derived from cell divisions of the cell in which the transposition event(s) occurred. This may therefore result in each of those cells displaying the same phenotypic variation. For example, if the transposition event has been induced in a cell from which some or all cells of a particular tissue of a particular organ is derived, the phenotypic consequences of the insertional event may be limited to the cells, the particular tissue or the particular organ. Where the transposition event has been induced in a cell from which only some of the cells of a particular tissue of a particular organ are derived, a milder phenotype may result from the transposition event than might be observed if all cells of the tissue display the transposition event. Where the transposition event is lethal to a cell, the cells will not survive. If the insertional event is present in all cells from which a particular tissue or organ is composed, that tissue or organ may not function or develop and the embryo may not be viable. Alternatively, the transposition event may have non-lethal phenotypic consequences. For example, the transposition event may have the effect of modulating the function of an enzyme in the affected cells, resulting in a relative change in metabolism compared to the unaffected cells. This may therefore result in an organ such as the liver, in which a sector of tissue of the variant phenotype is present adjacent to a sector of the same tissue of the normal phenotype or even a second variant phenotype. The distribution of the variant phenotype within an organism will thus depend on the stage of embryonic development at which transposition is induced. Moreover, in some embodiments of the invention induction of a "second round" of transposition may be useful in detecting either inversion of the phenotype, caused by excision of an element, or, more importantly, modification of the phenotype, caused by a new insertion to an interacting gene.

Phenotypic variations in cells, tissues or organs of the transgenic organisms may be traced back to transposition events in the genome of those cells, tissues or organs.

Accordingly, in a fourth aspect the invention provides a method for detecting and characterising a genetic mutation in a transgenic organism, comprising the steps of:
(a) generating a transgenic embryo and inducing transposition therein by a method according to the first or third aspect of the invention or a transgenic organism according to the second aspect of the invention;
(b) identifying in the transgenic embryo or offspring developed therefrom the presence of a plurality of cells displaying a variant phenotype;
(c) detecting the position of one or more transposon transposition events in the genome of one or more of the cells; and correlating the position of the transposition events with the observed variant phenotype, the position of the transposition events being indicative of the location of one or more genetic loci associated with the observed variant phenotype.

A "transposition event" is a change in genomic sequence caused by transposon mobilisation and includes insertion events, excision events or chromosomal breaks.

Insertion events may be detected by screening for the presence of the transposon by probing for the nucleic acid sequence of the transposon. Excisions may also be identified by the "signature" sequence left behind upon excision.

A fifth aspect of the invention provides a method for isolating a gene which is correlated with a phenotypic characteristic in a plurality of cells in a transgenic animal, comprising the steps of:
(a) generating a transgenic embryo and inducing transposition therein by a method according to the first or third aspect of the invention or a transgenic organism according to the second aspect of the invention;
(b) identifying in the transgenic embryo or offspring developed therefrom the presence of a plurality of cells displaying the phenotypic characteristic;
(c) detecting the position of one or more transposon transposition events in the genome of one or more of the cells; and
(d) cloning the genetic loci comprising the insertions.

The locus of the modification may be identified precisely by locating the transposon insertion. Sequencing of flanking regions allows identification of the locus in databases, potentially without the need to sequence the locus.

In preferred embodiments of the invention, the transposon may be a natural transposon. Preferably, it is a class 2 transposon, such as Minos. Most advantageously, it is Minos. Alternative transposons include mariner, Hermes, piggyBac, hobo and salmonid-type transposons such as Sleeping Beauty.

Modified transposons, which incorporate one or more heterologous coding sequences and/or expression control sequences may also be used in the invention. Such coding sequences may include selectable and/or unselectable marker genes, which may facilitate the identification of transposons in the genome and cloning of the loci into which the transposons have been integrated. Suitable markers include fluorescent and/or luminescent polypeptides, such as GFP and derivatives thereof, luciferase, β-galactosidase or chloramphenicol acetyl transferase (CAT).

Such markers may be used in in vivo enhancer or silencer traps and exon traps, by, for example inserting transposons which comprise marker genes which are modulated in their expression levels by proximity with enhancers or exons. Constructs for use in exon and enhancer traps are described in EP 0955364. Using the methods of the invention, the plurality of cells or tissues homogeneous for a transposition event may display modulation of expression of marker gene(s), thus enabling efficient trapping of enhancers and/or silencers and/or exons. Moreover, in embodiments where only a proportion of cells or tissues of a particular type are homogeneous for the transposition event, modulation of the expression of a marker gene may be identified by comparison with cells or tissues of the same type in the same transgenic animal which does not display such modulation.

Accordingly, the invention further provides in a sixth aspect a method for isolating an enhancer or a silencer in a transgenic animal, comprising the steps of:
(a) generating a transgenic embryo and inducing transposition therein by a method according to the first or third aspect of the invention or a transgenic organism according to the second aspect of the invention, wherein the transposon comprises a reporter gene under the control of a minimal promoter such that it is expressed at a basal level;
(b) assessing the level of expression of the reporter gene in one or more cells or tissues of the transgenic embryo or offspring derived therefrom;
(c) identifying and cloning genetic loci in one or more of the cells or tissues in which the modulation of the reporter gene is increased or decreased compared to the basal expression level; and
(d) characterising the cloned genetic loci in the cell or tissue.

In a seventh aspect, there is provided a method for isolating an exon in a transgenic animal, comprising the steps of:
(a) generating a transgenic embryo and inducing transposition therein by a method according to the first or third aspect of the invention or a transgenic organism according to the second aspect of the invention, wherein the transposon comprises a reporter gene which lack translation initiation sequences but includes splice acceptor sequences;
(b) identifying in the embryo or offspring derived therefrom one or more cells or tissues in which the reporter gene is expressed; and (c) cloning the genetic loci comprising the expressed reporter gene from the cells or tissues.

FIGS. 2, 3 and 4 schematically illustrate gene trap constructs which may be used in generating embryos for use in these aspects of the invention.

FIG. 2 illustrates a transposase construct which is under the control of the tet responsive element (TRE) linked to a minimal promoter and a transposon comprising a marker gene encoding an autofluorescent protein (AFP) under the control of a minimal promoter. In transgenic embryos comprising both constructs, expression of the transposase may be induced by activation of the inducible TetO promoter, such that the transposition of the transposon construct may be achieved. Integration into the genome at or near an enhancer site can be detected by expression of the marker gene.

FIG. 3 illustrates a transposase construct which is under the control of the inducible TetO promoter and a transposon comprising an AFP fluorescent reporter gene which lacks translation initiation sequences but includes splice acceptor sequences. In transgenic embryos comprising both constructs, expression of the transposase may be induced by activation of the inducible TetO promoter, such that the transposition of the transposon construct may be achieved. Integration into an intron in the appropriate orientation can be detected by expression of the marker gene.

In a preferred embodiment, transposons may be used to upregulate the expression of genes. For example, a transposon may be modified to include an enhancer or other transcriptional activation element. Mobilisation and insertion of such a transposon in the vicinity of a gene upregulates expression of the gene or gene locus. This embodiment has particular advantage in the isolation of oncogenes, which may be identified in clonal tumours by localisation of the transposon.

FIG. 4 illustrates a gene activation system which may be used in generating embryos for use in this aspect of the invention. FIG. 4 illustrates a transposase construct which is under the control of the inducible TetO promoter and a transposon comprising an AFP fluorescent marker gene similarly under the control of the inducible TetO promoter. In transgenic embryos comprising both constructs, expression of the transposase may be induced by activation of the inducible TetO promoter, such that the transposition of the transposon construct may be achieved. Further, if the transposed construct comprising the AFP is inserted upstream of an ectopic gene, the gene may be activated and its phenotypic effect observed upon induction of the TetO promoter.

In conventional methods of inducing genetic modifications by transposition, in which a mosaic of cells each of which may have unique transposition induced genetic modifications is produced, the study of the phenotypic results of each transposition event is difficult. Similarly, the study of the effects of natural and artificial stimuli on the transposed cells is difficult to perform and to interpret. However, in contrast, as the methods of the invention enable the production of transgenic embryos and organisms in which one or more cluster of cells or tissues is homogeneous for a single transposition event, the effect of a pharmacological or natural stimulus may be easily observed, e.g. by comparison of reporter gene expression in a homogeneous cluster of cells with that in surrounding cells or tissues. Thus, the methods of the invention may be used to study the response of cells in which transposition events have occurred to natural stimuli such as physiological stimuli, for example, hormones, cytokines and growth factor or artificial stimuli such as drugs in drug discovery approaches, toxicology studies and the like. Indeed, the methods of the invention enable the response of a cluster of cells or tissues to a stimulus to be observed in real time.

Accordingly, in an eighth aspect of the invention, there is provided a method for identifying a gene responsive to a stimulus in a transgenic animal comprising the steps of:
(a) generating a transgenic embryo and inducing transposition therein by a method according to the first or third aspect of the invention or a transgenic organism according to the second aspect of the invention, wherein the transposon comprises a reporter gene under the control of a minimal promoter such that it is expressed at a basal level;
(b) assessing the level of expression of the reporter gene in one or more cells or tissues of the of the transgenic embryo or offspring derived therefrom in the absence of the stimulus;
(c) providing the stimulus;
(d) identifying and cloning genetic loci in one or more of the cells or tissues in which the modulation of the reporter gene is increased or decreased in response to the stimulus compared to the basal expression level.

The method may further comprise the additional step:
(e) characterising the cloned genetic loci in the cell or tissue.

This aspect of the invention may thus be used in the identification of novel targets for molecular intervention, including targets for disease therapy in humans, plants or animals, development of insecticides, herbicides, antifungal agents and antibacterial agents.

One further application is the discovery of genes responsible for pathogenesis (for example, in mouse disease models). If activation of a gene, (e.g. a kinase or a receptor) is involved in the pathogenesis of the disease, it is possible that, for example, 50% inactivation of the gene will alleviate or reverse one or more phenotypes of the disease. Therefore, groups of cells with an insertion of a transposon which inactivates one of the two copies of such a gene will be detectable as healthy clusters in a diseased background.

The transposon may be inserted into a gene. Preferably, the transposon is inserted into a transcribed gene, resulting in the localisation of the transposon in open chromatin. The transposon may be flanked by chromatin opening domain elements, such as locus control regions which provide tissue specific expression (Fraser, P. & Grosveld, F. (1998) *Curr Opin Cell Biol* 10:361-365) or ubiquitously-acting chromatin opening elements—(UCOEs), which enable non-tissue specific expression (for example see WO 0005393). Other chromatin opening domains which may be used in methods of the invention include CpG rich islands, which may normally be associated with housekeeping genes or tissue specific genes, or insulators.

Moreover, the transposon may itself comprise, between the transposon ends, chromatin opening domains. This will cause activation of the chromatin structure into which the transposon integrates, facilitating access of the inducible transposase in a cell or tissue specific manner thereto.

Similarly the transposase construct may comprise or be flanked by chromatin opening domain elements.

The ability to regulate the transposition event during embryo development and adult life increases the likelihood of transposition events in multiple chromatin domains present in different tissues during different times of development.

The methods of the invention may advantageously be used in the generation of a library of genetically modified organisms, in each of which one or more populations of cells or tissues are homogeneous for a genetic modification produced by transposon mobilisation at a predetermined stage of development. Thus, in a further aspect of the invention, there is provided a method for producing a library of transgenic organisms in each of which one or more populations of cells or tissues are homogeneous for a gene modified by transposon mobilisation, comprising modifying cells by transposon mobilisation by the method according to a first or second or third aspect of the invention, wherein step (1) is performed at the predetermined stage of embryo development.

A library of transgenic organisms produced by such a method forms a further aspect of the invention.

In one embodiment of the invention, the at least one of the one or more regulatory sequences which permit expression of the transposase are sequences derived from a sperm specific promoter.

In one embodiment of the invention the nucleotide sequence of the gene encoding the transposase has been mammalianized.

According to the methods of the invention, the activity of the transposase can be increased or maximized in a target organism by methods well known in the art including but not limited to optimizing codon usage to the target organism (for example mouse or rat), as described hereinbelow, increasing the copy number of the transposase gene, or engineering the transposase to increase or maximise activity in a target organism. The activity of a transposase can be increased by protein engineering methods well known in the art.

In one embodiment of the invention the nucleotide sequence of the gene encoding the transposon has been modified to optimize codon usage.

In one embodiment, the nucleotide sequence of the gene encoding the transposon has been mammalianized.

In one embodiment of the invention transposition occurs in the sperm, the egg or the early embryo.

In one embodiment of the invention expression of the gene encoding the transposase is eliminated by gene excision at a lox site by cre or at an FRT site by FLP.

As used herein "one or more copies", as it refers to a transposon or a transposase of the invention, means 1-10, preferably 1-20, more preferably 1-50 and most preferably 1-100 or more, ((for example, 1, 2, 3, 4, 5, 6, 7, 8, 9, 10, 20, 30, 40, 50, 60, 70, 80, 90, 100, 200, 300, 400, 500 or more). In one embodiment the "one or more copies" of the transposon are integrated in tandem at one or more sites, as defined herein, in the genome (i.e. on different chromosomes).

In one embodiment of the invention, the first adult transgenic organism and/or the progeny comprises between 1 and 100 copies of the transposon.

In one embodiment of the invention the second adult transgenic organism and/or the progeny comprises between 1 and 100 copies of said transposase.

In one embodiment the one or more copies of a transposon are integrated at one or more sites in the genome of the first adult organism and/or the progeny.

In one embodiment the nucleotide sequence of the gene encoding the transposase is modified to increase transposase activity in said progeny. As used herein, "increase" means the activity is at least 5% or more greater than (for example, 5, 6, 7, 8, 9, 10, 20, 30, 40, 50, 60, 70, 80, 90 or 100% greater than) the activity of an unmodified transposase.

As used herein, "modified or engineered" refers to altering the polynucleotide or amino acid sequence, for example, of a transposase of the invention. The polynucleotide encoding a transposase can comprise coding sequences for a naturally occurring transposase or can encode an altered transposase with increased activity, as defined herein, as compared to a naturally occurring transposase. In one embodiment, a polynucleotide sequence encoding a transposase is modified by introducing one or more mutations. A mutation or mutations in a transposase polynucleotide can be made by site directed mutagenesis using conventional techniques. A library of mutant polynucleotides comprising single, double, or higher mutations, can also be prepared using random mutagenesis techniques. Mutagenesis techniques are described generally, e.g., in Current Protocols in Molecular Biology, Ausubel, F. et al. eds., John Wiley (1998), and random mutagenesis (also referred to as "DNA shuffling") is the subject of U.S. Pat. Nos. 5,605,793, 5,811,238, 5,830,721, 5,834,252 and 5,837,458 to Stemmer et al.

As used herein "mutation" refers to a variation in the nucleotide sequence of a gene or regulatory sequence as compared to the naturally occurring or normal nucleotide sequence. A mutation may result from the deletion, insertion or substitution of more than one nucleotide (e.g., 2, 3, 4, or more nucleotides) or a single nucleotide change such as a deletion, insertion or substitution. The term "mutation" also encompasses chromosomal rearrangements.

As used herein, "alteration" refers to a change in either a nucleotide or amino acid sequence, as compared to the naturally occurring sequence, resulting from a deletion, an insertion or addition, or a substitution.

As used herein, "deletion" refers to a change in either nucleotide or amino acid sequence wherein one or more nucleotides or amino acid residues, respectively, are absent.

As used herein, "insertion" or "addition" refers to a change in either nucleotide or amino acid sequence wherein one or more nucleotides or amino acid residues, respectively, have been added.

As used herein, "substitution" refers to a replacement of one or more nucleotides or amino acids by different nucleotides or amino acid residues, respectively.

A polynucleotide comprising mutations of a transposase of the invention can also be synthesized in a laboratory. Alternatively the transposase may comprise one or more insertions, substitutions or deletions of amino acids to provide enhanced activity in the host organism.

In one embodiment, a transposase polynucleotide of the invention is engineered such that the codons are systematically replaced by codons preferred by the target organism. For example, the coding sequence of a transposase, or a portion thereof, can be analyzed for its codon usage. This codon usage can then be compared with the frequency of codon usage in abundant proteins found in a target organism. The codons of a transposase which have low or zero frequency of use in a target organism can be modified by, for example, site directed mutagenesis or a polynucleotide can be synthesized in the laboratory. The codon modifications are made to conform with the codons used in the genes for the abundantly expressed target organism proteins. Further, segments of codons with poly-A signal sequences can be modified to other codons for the same amino acids. Further, cryptic signal sequences, intron splice sites, and potential methylation sites can be modified. A transposase polynucleotide sequence which as had at least 1 or more (for example 1, 2, 3, 4, 5, 10, 20, 50, 60, 70, 80, 90, 100, 200, 300 or more) codons modified to target organism preferred codons is said to be optimized for codon usage in a target organism. In one embodiment, optimization for codon usage in a target organism further comprises modification of codons encoding possible signal sequences, intron splice sites, and methylation sites.

BRIEF DESCRIPTION OF THE FIGURES

FIG. 6 illustrates the structure of the Minos transposase expression cassette which may be used in an embodiment of the invention as described in Example 4. The 6.5 kb 5' flanking region and promoter of the ZP3 gene were joined to Minos transposase cDNA (ILMi) and the second intron and polyadenylation site of the human β globin gene. The relevant restriction sites are indicated.

FIG. 11 illustrates knock-in (A) and regular constructs (B) for specific expression of transposase in sperm or egg or for ubiquitous expression. In FIG. 11B, the beta globin 3' second exon (red), intervening sequences (green) and third exon (red) are added.

FIG. 16 is a diagram depicting generation of a double positive transposon/transposase transgenic male.

FIG. 17 is a diagram showing mousified Minos transposase knocked into H1t.

FIG. 21 shows the results of FISH analysis of transposition events.

DETAILED DESCRIPTION OF THE INVENTION

Figure 1:
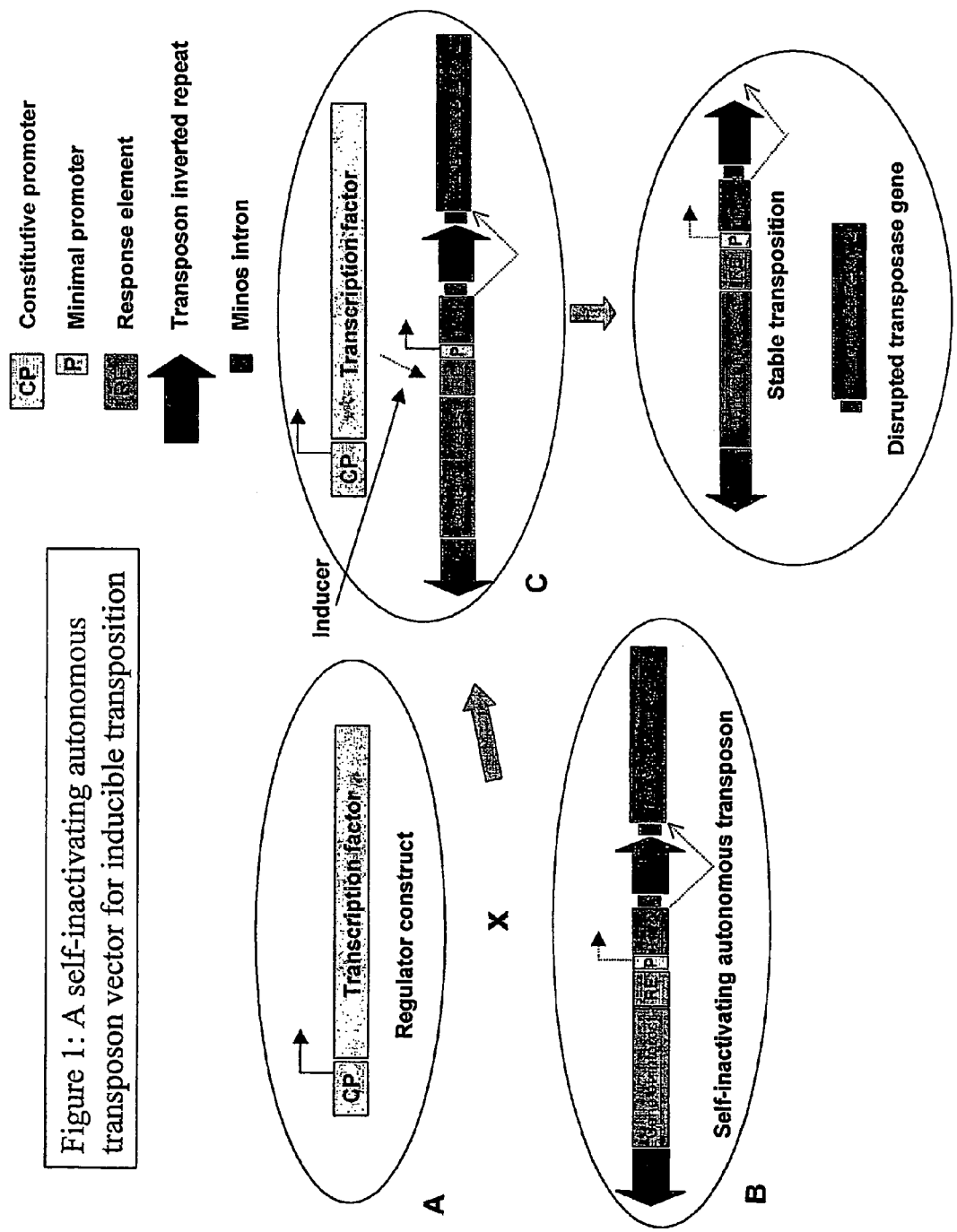
FIG. 1 illustrates schematically, the use of a self-inactivating autonomous transposon construct in an embodiment of the invention. A first transgenic organism (A), the genome of which comprises a regulator construct, is crossed with a second transgenic organism (B), the genome of which comprises a transposon comprising a gene of interest. One of the inverted repeats of the transposon is positioned in an intron which interrupts the transposase gene. On inducing mobilisation of the transposon in the progeny of the cross (C) the transposase gene is disrupted, resulting in stabilised transposition of the gene of interest with no further transposition events, even in the presence of inducer.
Figure 2:
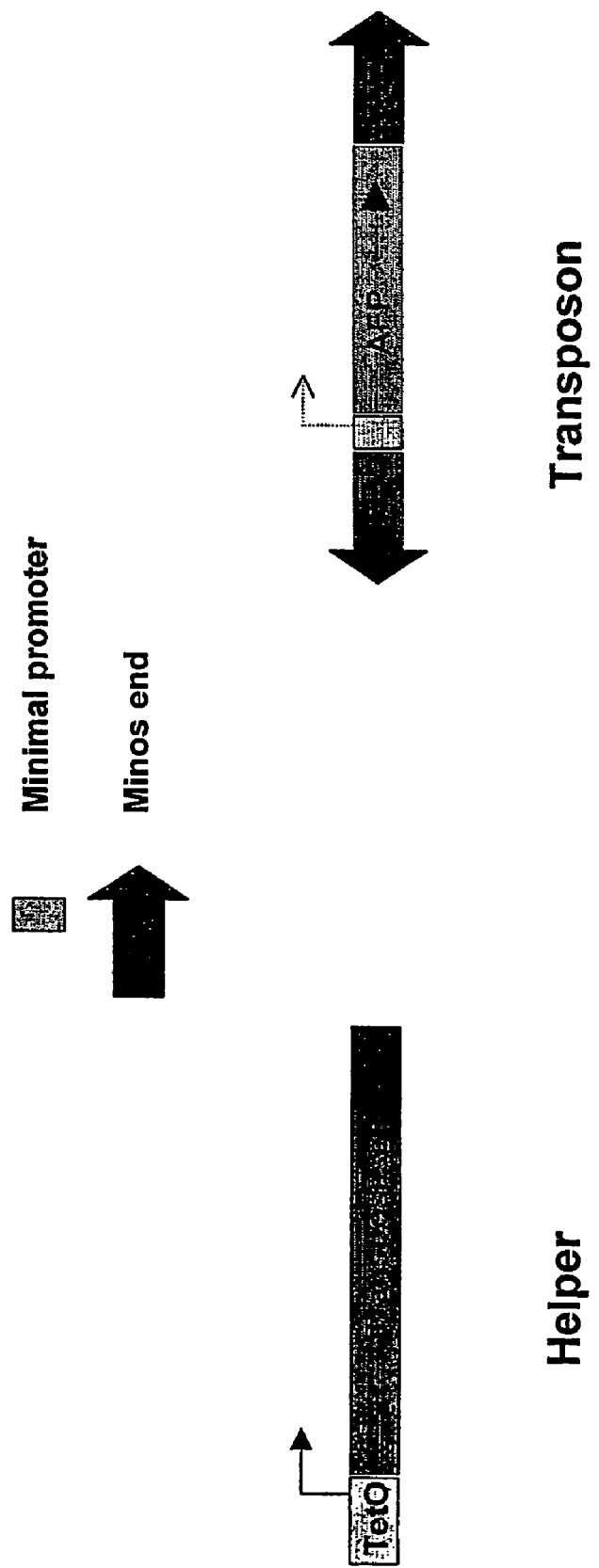
FIG. 2 shows schematically a transposase encoding construct in which the transposase gene is under the control of the inducible TetO promoter and a transposon comprising an AFP fluorescent marker gene under the control of a minimal promoter for use in enhancer trap methods of the invention.
Figure 3:
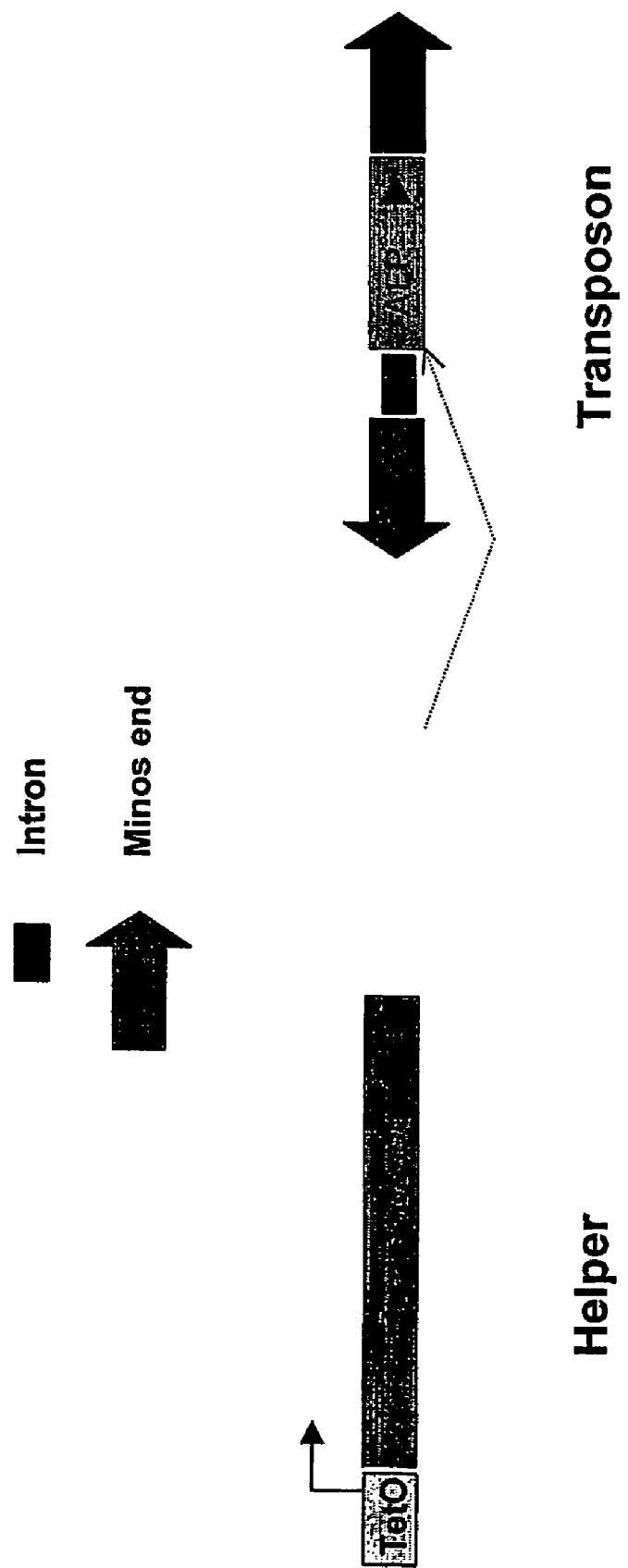
FIG. 3 illustrates a transposase construct which is under the control of the inducible TetO promoter and a transposon comprising an AFP fluorescent reporter gene which lacks translation initiation sequences but includes splice acceptor sequences for use in exon trap methods of the invention.
Figure 4:
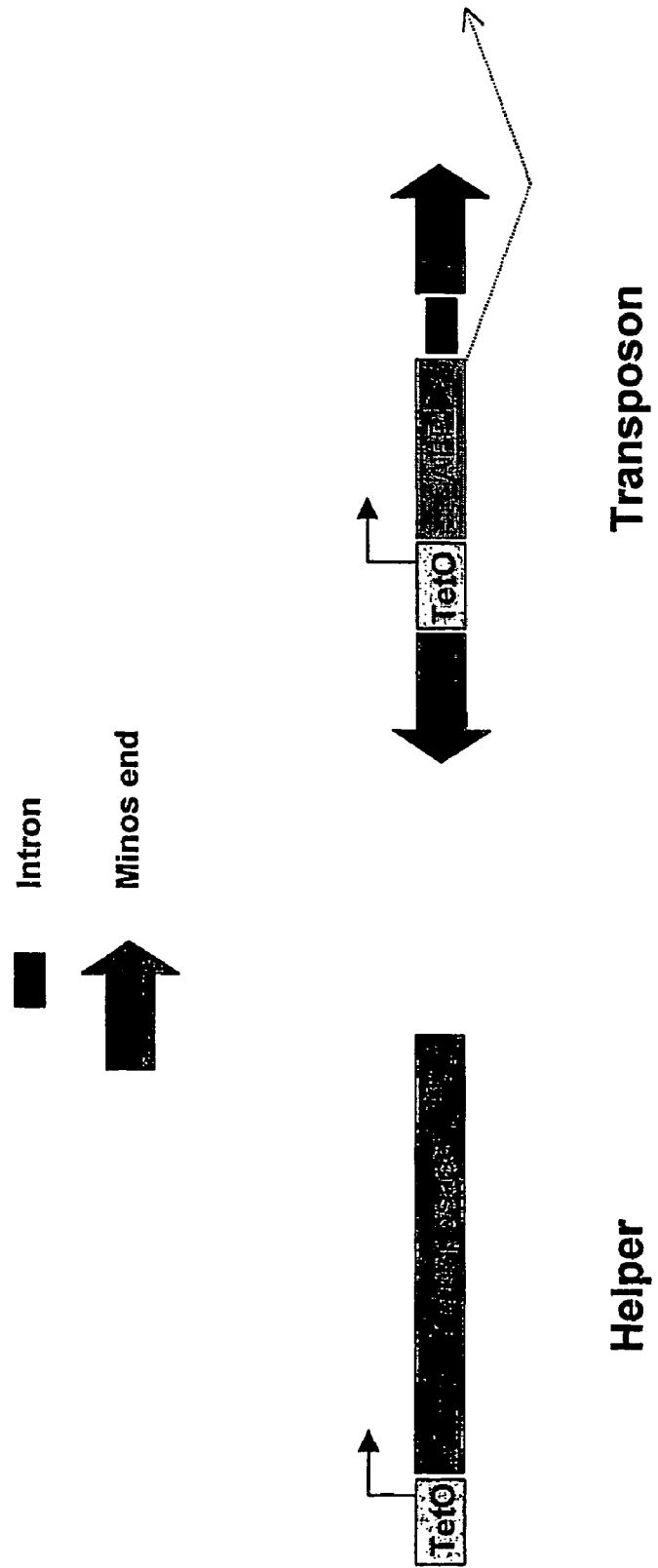
FIG. 4 shows schematically a transposase construct and a transposon for use in gene traps to identify ectopic genes.

Although in general the techniques mentioned herein are well known in the art, reference may be made in particular to Sambrook et al., Molecular Cloning, A Laboratory Manual (1989) and Ausubel et al., Short Protocols in Molecular Biology (1999) $4^{th}$ Ed, John Wiley & Sons, Inc.

Transposons

Any transposon may be used in the method of the invention. Preferably, the transposon is type 2 transposon, more preferably selected from the group consisting of Minos, mariner, Hermes, piggyBac, and Sleeping Beauty. Advantageously, the transposon is Minos. Each transposon is advantageously employed with its natural cognate transposase, although the use of modified and/or improved transposases, for example, a mammalianized transposon, is envisaged. Minos transposons, and their cognate transposase, are described in detail in U.S. Pat. No. 5,840,865 and European patent application EP 0955364.

The transposon preferably comprises a nucleic acid sequence encoding a heterologous polypeptide. This sequence will be integrated, together with the transposon, into the genome of the cell on transposon integration. Moreover, it will be excised, together with the transposon, when the latter excises on remobilisation. In a preferred embodiment, the heterologous polypeptide is a selectable marker. This allows cells having integrated transposons to be identified and the site of integration to be accurately mapped.

Marker Genes

Preferred marker genes include genes which encode fluorescent polypeptides. For example, green fluorescent proteins ("GFPs") of cnidarians, which act as their energy-transfer acceptors in bioluminescence, can be used in the invention. A green fluorescent protein, as used herein, is a protein that fluoresces green light, and a blue fluorescent protein is a protein that fluoresces blue light. GFPs have been isolated from the Pacific Northwest jellyfish, *Aequorea victoria*, from the sea pansy, *Renilla reniformis*, and from *Phialidium gregarium*. (Ward et al. (1982) *Photochem Photobiol* 35:803-808; Levine et al. (1982) *Comp Biochem Physiol* 72B:77-85). Fluorescent proteins have also been isolated recently from *Anthoza* species (accession nos. AF168419, AF168420, AF168421, AF168422, AF168423 and AF168424).

A variety of *Aequorea*-related GFPs having useful excitation and emission spectra have been engineered by modifying the amino acid sequence of a naturally occurring GFP from *Aequorea Victoria* (Prasher et al. (1992) *Gene* 111:229-233; Heim et al. (1994) *Proc Natl Acad Sci USA* 91:12501-12504; PCT/US95/14692). *Aequorea*-related fluorescent proteins include, for example, wild-type (native) *Aequorea Victoria* GFP, whose nucleotide and deduced amino acid sequences are presented in Genbank Accession Nos. L29345, M62654, M62653 and others *Aequorea*-related engineered versions of Green Fluorescent Protein, of which some are listed above. Several of these, i.e., P4, P4-3, W7 and W2 fluoresce at a distinctly shorter wavelength than wild type.

Examples of other marker genes which may be used include selectable marker genes such as genes encoding neomycin, puromycin or hygromycin or counter-selection genes such as the genes for cytosine deaminase or nitroreductase.

Those skilled in the art are aware of a multitude of marker genes which may be used. Any suitable marker gene may be used and it should be appreciated that no particular choice is essential to the present invention.

Identification of Insertion and Excision Events

Transposons, and sites from which transposons have been excised, may be identified by sequence analysis. For example, Minos typically integrates at a TA base pair, and on excision leaves behind a duplication of the target TA sequence, flanking the four terminal nucleotides of the transposon. The presence of this sequence, or related sequences, may be detected by techniques such as sequencing, PCR and/or hybridisation. The original insertion site of the transposon is, in one embodiment, additionally marked by *Drosophila* sequences flanking the transposon. These sites are still present at the original site of the transposon integration.

Inserted transposons may be identified by similar techniques, for example using PCR primers complementary to the terminal repeat sequences.

Transposases

Effective transposon mobilisation depends on both efficient delivery of the transposable element itself to the host cell and the presence of an effective cognate transposase in the cell in order to catalyse transposon jumping. A "cognate" transposase, as referred to herein, is any transposase which is effective to activate transposition of the transposon, including excision of the transposon from a first integration site and/or integration of the transposon at a second integration site. Preferably, the cognate transposase is the transposase which is naturally associated with the transposon in its in vivo situation in nature. However, the invention also encompasses modified transposases, which may have advantageously improved activities within the scope of the invention. For example, the sequence of the gene encoding the transposase may be modified to optimise codon usage and thus increase transposition frequencies. In one embodiment, the sequence is mammalianized. Optimisation of codon usage is a method well known in the art to increase the expression levels of a given gene. Alternatively the transposase may comprise one or more insertions, substitutions or deletions of amino acids to provide enhanced activity in the host organism.

The gene encoding the transposase may be provided in the genome of a second organism which is crossed with a first organism comprising, in its genome, the transposon to produce a double positive embryo for use in the methods of the invention. In an alternative embodiment, one or more copies of both the transposon and the gene encoding the cognate transposase are provided in the genome of a first organism, which may be crossed with a second organism comprising one or more copies of regulatory elements necessary to permit inducible transposase expression to produce an embryo.

A number of methods are known in the art for introduction of a gene into the genome of a host cell, and may be employed in the context of the present invention. For example, transposase genes may be inserted into the host cell genome by transgenic techniques. Such methods are discussed further below.

Regulation of Transposase Expression

Coding sequences encoding the transposase may be operatively linked to regulatory sequences which modulate transposase expression as desired. Control sequences operably linked to sequences encoding the transposase include promoters/enhancers and other expression regulation signals. These control sequences may be selected to be compatible with the host organism in which the expression of the transposase is required. The term promoter is well known in the art and encompasses nucleic acid regions ranging in size and complexity from minimal promoters to promoters including upstream elements and enhancers.

The promoter is typically selected from promoters which are functional in cell types homologous to the organism in question, or the genus, family, order, kingdom or other classification to which that organism belongs, although heterologous promoters may function—e.g. some prokaryotic promoters are functional in eukaryotic cells. The promoter may be derived from promoter sequences of viral or eukaryotic genes. For example, it may be a promoter derived from the genome of a cell in which expression is to occur. With respect to eukaryotic promoters, they may be promoters that function in a ubiquitous manner (such as promoters of α-actin, β-actin, tubulin) or, alternatively, a tissue-specific manner (such as promoters of the genes for pyruvate kinase). In the generation of germline transposition events, the promoters may be derived from genes whose expression is induced during gametogenesis, either oogenesis or spermatogenesis. Alternatively, for developmentally regulated transposition events such as transposition during zygote development, the promoters may be derived from genes whose expression is developmentally regulated. For expression in the early zygote, promoters from maternal effect genes may be used. They may also be promoters that respond to specific stimuli, for example promoters that bind steroid hormone receptors. Viral promoters may also be used, for example the Moloney murine leukaemia virus long terminal repeat (MMLV LTR) promoter, the rous sarcoma virus (RSV) LTR promoter or the human cytomegalovirus (CMV) IE promoter.

According to the invention, the gene encoding the transposase is under the control of one or more regulatory sequences, meaning that the levels of expression obtained using e.g. a promoter can be regulated. For example the regulatory sequence may be an inducible regulatory sequence.

Inducible systems for gene expression are known in the art, and include tetracycline, ecdysone and estrogen-inducible systems or the lac operator-repressor system.

A widely used system of this kind in mammalian cells is the tetO promoter-operator, combined with the tetracycline/doxycycline-repressible transcriptional activator tTA, also called Tet-Off gene expression system (Gossen, M. & Bujard, H. (1992) Tight control of gene expression in mammalian cells by tetracycline responsive promoters. *Proc Natl Acad Sci USA* 89:5547-5551), or the doxycycline-inducible rtTA transcriptional activator, also called Tet-On system (Gossen, M., Freundlieb, S., Bender, G., Muller, G., Hillen, W. & Bujard, H. (1995) Transcriptional activation by tetracycline in mammalian cells. *Science* 268:1766-1769).

In the Tet-Off system, gene expression is turned on when tetracycline (Tc) or doxycycline (Dox; a Tc derivative) is removed from the culture medium. In contrast, expression is turned on in the Tet-On system by the addition of Dox. Procedures for establishing cell lines carrying the transcriptional activator gene and the Tet-regulatable gene stably integrated in its chromosomes have been described. For example see http://www.clontech.com/techinfo/manuals/PDF/PT3001-1.pdf. For example, the Tet-On system may be employed for tetracycline-inducible expression of Minos transposase in a transgenic animal.

A doubly transgenic animal may be generated by methods well known in the art including but not limited to transgenesis (microinjection of oocytes), transfection of ES cells or standard homologous recombination ES cell technology. Both transgenesis and transfection result in random integration in the genome but transfection can also be used for a homologous integration by standard techniques. Two constructs are used: first, a construct containing the rtTA gene under a constitutive promoter. An example of such construct is the pTet-On plasmid (Clontech) which contains the gene encoding the rtTA activator under control of the Cytomegalovirus immediate early (CMV) promoter. The rtTA transcriptional activator encoded by this construct is active only in the presence of Doxycycline. The second construct contains the Minos transposase gene under control of the tetracycline-response element, or TRE. The TRE consists of seven direct repeats of a 42-bp sequence containing the tet operator (tetO), and is located just upstream of the minimal CMV promoter, which lacks the enhancer elements normally associated with the CMV immediate early promoter. Because these enhancer elements are missing, there is no "leaky" expression of transposase from the TRE in the absence of binding by rtTA. An example of such construct is the pTRE2 plasmid (Clontech) in the MCS of which is inserted the gene encoding Minos transposase. In cells stably transformed with the two constructs, rtTA is expressed but does not activate transcription of Minos transposase unless Doxycycline is administered to the animal.

Therefore, when, according to a method of the invention, a transgenic animal comprising both pTet-On and the pTRE2 constructs is crossed with another animal, the genome of which comprises a transposon, mobilisation of transposons in resulting embryos comprising within their genomes both the transposon and the gene encoding the transposase will not occur in the absence of Doxycycline. Administration of Doxycycline thus be used to induce transposition.

Inducers, e.g. Doxycycline, may be administered to embryos by any suitable method. In a preferred embodiment of the invention, inducers of transposase expression are administered via the food or water of the parent organism.

Alternative inducible systems include tamoxifen inducible transposase [a modified oestrogen receptor domain (Indra et al., Nucl Acid Res. 27, 4324-27, 1999) coupled to the transposase which retains it in the cytoplasm until tamoxifen is given to the culture], an RU418 inducible transposase (operating under the same principle with the glucocorticoid receptor; see Tsujita et al., J Neuroscience, 19, 10318-23, 1999), or an ecdysone-inducible system.

The ecdysone-inducible system is based on the heterodimeric ecdysone receptor of *Drosophila*, which is induced by the insect hormone, ecdysone and its derivatives. During metamorphosis of *Drosophila melanogaster*, a cascade of morphological changes is triggered by the steroid hormone 20-OH ecdysone, generally referred to as "ecdysone", via the ecdysone receptor. Ecdysone responsiveness may be transferred to mammalian cells by the stable expression of a modified ecdysone receptor that regulates an optimized ecdysone responsive promoter. Transgenic organisms, e.g. mice expressing the modified ecdysone receptor can activate an integrated ecdysone responsive promoter upon administration of hormone or its derivatives e.g. Once the receptor binds ecdysone or muristerone, an analog of ecdysone, the receptor activates the ecdysone-responsive promoter to give controlled expression of the gene of interest. Ecdysone-based inducible systems are reported to exhibit lower basal activity and higher inducibility than tetracycline based systems. Further details of ecdysone based inducible systems can be found, for example, in U.S. Pat. No. 6,245,531 and in No D, Yao T P, Evans RM Ecdysone-inducible gene expression in mammalian cells and transgenic mice, Proc Natl Acad Sci USA 1996 April 93:3346-51, the contents of each of which are herein incorporated by reference.

The lac operator-repressor system has recently been shown to be functional in mammals, in particular the mouse. Cronin et al, Genes and Development, 15, 1506-1517 (2001), the contents of which are herein incorporated by reference, describes the use of a lac repressor transgene that resembles a typical mammalian gene both in codon usage and structure and that expresses functional lac repressor protein ubiquitously in mice to control the expression of a reporter gene under the control of the lac promoter. Expression of the reporter gene is reversible using the lactose analog IPTG provided in the drinking water of the mouse or mother of the embryo or nursing pup. The lac operator-repressor system may thus be adapted for use to regulate expression of the transposase by placing the transposase gene under the control of a lac promoter.

In addition, any of these promoters may be modified by the addition of further regulatory sequences, for example enhancer sequences. Chimeric promoters may also be used comprising sequence elements from two or more different promoters described above.

The use of locus control regions (LCRs) is also envisaged. LCRs are capable of conferring tightly-regulated tissue specific control on transgenes, and to greatly increase the fidelity of transgene expression. A number of LCRs are known in the art. These include the β-globin LCR (Grosveld et al., (1987) Cell 51:975-985); α-globin (Hatton et al., (1990) Blood 76:221-227; and CD2 (Festenstein et al., (1996) Science 271: 1123-1125) the T cell specific CD4 (Boyer et al J Immunol 1997, 159:3383-3390), and TCR loci (Diaz P, et al Immunity 1994, 1:207-217; Ortiz et al EMBO J 1997, 16:5037-5045; Hong et al Mol Cell Biol 1997, 17:2151-2157.) the B-cell-specific MHC class II Ea (Carson et al Nucleic Acids Res 1993, 21:2065-2072), the macrophage-specific lysozyme gene (Bonifer et al EMBO J 1990, 9:2843-2848), the neuron-specific S100 gene (Friend et al J Neurosci 1992, 12:4337-4346), the liver-specific LAP gene (Talbot et al Nucleic Acids Res 1994, 22:756-766), the human growth hormone locus (Jones et al Mol Cell Biol 1995, 15:7010-7021), plus immunoglobulins, muscle tissue, and the like. Further details on LCRs are provided in Fraser, P. & Grosveld, F. (1998). Curr. Opin. Cell Biol. 10, 361-365 and Li, Q., Harju, S. & Peterson, K. R. (1999). Trends Genet. 15:403-408.

Alternatively, gene domains that need to be open and switched-on in all cells of the body; i.e. gene domains whose proteins (such as enzymes for generating energy from sugars), are needed by all cells for survival and which are therefore ubiquitously expressed may be exploited to enable expression of the transposon and/or transposase in every tissue. Examples of such ubiquitously-acting chromatin opening elements —(UCOEs) include the human genes known as TBP and hnRNPA2. Further details of the use of such UCOEs may be found in Antoniou, M. and Grosveld, F. (1999). (Genetic approaches to therapy for the haemoglobinopathies. in: Blood Cell Biochemistry, Volume 8: Hematopoiesis and Gene Therapy Fairbairn and Testa eds. Kluwer Academic/Plenum Publishers, New York. pp 219-242) and in PCT/GB99/02357 (WO 0005393), the contents of both of which are herein incorporated by reference.

Regulation of transposase and/or transposon expression may also be achieved through the use of ES cells. Using transformed ES cells to construct chimeric embryos, it is possible to produce transgenic organisms which contain the transposase genes or transposon element in only certain of their tissues. This can provide a further level of regulation.

Maximising Efficiency of Transposition

As described above and for example, in WO 01/71019 and WO 02/062991, transposition is achieved by the action of the transposase enzyme on the terminal repeat sequences of the integrated transposon, resulting in excision of the transposon from its original position in the "host" genome and reinsertion of the transposon at a different position in the genome.

As with most biochemical processes, this process can be made to be more efficient by simply improving the concentration of substrates, high levels of the terminal repeats sequences, i.e. an increase in copy number and high levels of the transposase enzyme.

An increase in copy number can be achieved by generating multiple copy arrays at the original insertion site. For example, 10 to 100 copies can be generated through standard transgenesis or using a PAC vector. Alternatively, multiple copies can be generated by the presence of multiple insertions at different sites in the genome.

The sequence of the transposase may be modified to optimise codon usage and thus, increase transposition frequencies. Optimisation of codon usage is a method well known in the art to increase the expression levels of a given gene.

Thus, the efficiency of the fly transposase in mammalian cells or animals may be increased by increasing its concentration as a result of a more efficient translation from mRNA by replacing the fly codon usage to mammalian codon usage.

Assays for determining transposase efficiency can include a standard transposition assay as described, for example, by Klinakis et al.; Insect Molecular Biology, 9 (3), 269-275, 2000.

The concentration of transposase mRNA can also be increased by including in the transposase mRNA sequence 5' and 3' sequences found in abundant stable mRNAs such as those encoding growth hormone, globin, actin or albumin.

Transgenic Organisms

Methods of the invention may employ one or more transgenic organisms having integrated in the genome the transposon, a gene encoding the cognate transposase or both.

The introduction of the transposon or gene encoding the transposase may be accomplished by any available technique, including transformation/transfection, delivery by viral or non-viral vectors and microinjection. Each of these techniques is known in the art. The transposon and the gene encoding the transposase may be inserted using the same or different methods. For example, the Drosophila P-element may be used to introduce a Minos transposase construct into Drosophila.

In a preferred embodiment, the transposon or gene encoding the transposase may be inserted into the host cell genome by transgenic techniques, for example to produce a transgenic animal comprising a transposon, a gene encoding a cognate transposase or both. Where the transgenic animal comprises both the transposon and the gene encoding the transposase, both constructs can be inserted using the same or different methods. Where delivery of the construct is by viral vector, a composite vector comprising both the transposon and the gene encoding the transposase under the control of a control sequence such as the Tet operator may be used. Alternatively, separate vectors may be used.

Any suitable transgenic animal may be used in the present invention. Animals include animals of the phyla cnidaria, ctenophora, platyhelminthes, nematoda, annelida, mollusca, chelicerata, uniramia, crustacea and chordata. Uniramians include the subphylum hexapoda that includes insects such as the winged insects. Chordates include vertebrate groups such as mammals, birds, fish, reptiles and amphibians. Particular examples of mammals include non-human primates, cats, dogs, ungulates such as cows, goats, pigs, sheep and horses and rodents such as mice, rats, gerbils and hamsters.

Techniques for producing transgenic animals which may be used in the method of the invention are well known in the art. A useful general textbook on this subject is Houdebine, Transgenic animals—Generation and Use (Harwood Academic, 1997)—an extensive review of the techniques used to generate transgenic animals.

In a preferred embodiment, the animal is an insect. Methods for producing transgenic insects which may be used in the method of the invention are well known (see for example Loukeris et al. (1995), Science 270, 2002-2005). Briefly, a transposable element carrying the gene of interest is inserted into a preblastoderm embryo using e.g. microinjection. Preferably, the new genetic material is placed at the polar plasm, which is the section of egg destined to become the still nascent insect's own egg or sperm cells. After many divisions of the nuclear material, most of it segregates to the periphery where it will become the nuclei of the insect's body. A small number of nuclei migrate to the pole to become egg cells on maturity. If these cells incorporate the transgene, progeny will be transgenic. Further details of producing transgenic insects are provided in Loukeris et al (1995), Science 270, 2002-2005 and O'Brochta and Atkinson (1998) Scientific American 279, 60-65.

In another preferred embodiment, the animal is preferably a mammal. Advances in technologies for embryo micromanipulation now permit introduction of heterologous DNA into, for example, fertilised mammalian ova. For instance, totipotent or pluripotent stem cells can be transformed by microinjection, calcium phosphate mediated precipitation, liposome fusion, retroviral infection or other means, the transformed cells are then introduced into the embryo, and the embryo then develops into a transgenic animal. In a highly preferred method, developing embryos are infected with a retrovirus containing the desired DNA, and transgenic animals produced from the infected embryo. In a most preferred method, however, the appropriate DNAs are coinjected into the pronucleus or cytoplasm of embryos, preferably at the single cell stage, and the embryos allowed to develop into mature transgenic animals after transfer into pseudopregnant recipients. Those techniques are well known (see reviews of standard laboratory procedures for microinjection of heterologous DNAs into mammalian fertilised ova, including Hogan et al., Manipulating the Mouse Embryo, (Cold Spring Harbor Press 1986); Krimpenfort et al., Bio/Technology 9:844 (1991); Palmiter et al., Cell, 41:343 (1985); Kraemer et al., Genetic manipulation of the Mammalian Embryo, (Cold Spring Harbor Laboratory Press 1985); Hammer et al., Nature, 315:680 (1985); Wagner et al., U.S. Pat. No. 5,175,385; Krimpenfort et al., U.S. Pat. No. 5,175,384, the respective contents of which are incorporated herein by reference).

Transgenic animals may also be produced by nuclear transfer technology as described in Schnieke, A. E. et al., 1997, Science, 278: 2130 and Cibelli, L B. et al., 1998, Science, 280: 1256. Using this method, fibroblasts from donor animals are stably transfected with a plasmid incorporating the coding sequences for a polypeptide of interest under the control of regulatory sequences. Stable transfectants are then fused to enucleated oocytes, cultured and transferred into female recipients.

Analysis of animals which may contain transgenic sequences would typically be performed by either PCR or Southern blot analysis following standard methods.

By way of a specific example for the construction of transgenic mammals, such as cows, nucleotide constructs comprising a sequence encoding a DNA binding molecule are microinjected using, for example, the technique described in U.S. Pat. No. 4,873,191, into oocytes which are obtained from ovaries freshly removed from the mammal. The oocytes are aspirated from the follicles and allowed to settle before fertilisation with thawed frozen sperm capacitated with heparin and prefractionated by Percoll gradient to isolate the motile fraction.

The invention provides for transgenic animals produced by any method known in the art. For example, transgenic animals useful according to the invention are produced by methods including but not limited to 1) microinjection of fertilized eggs; 2) transfection or infection of ES cells followed by injection of ES cells into blastocysts, resulting in chimeric offspring, or fusion of ES cells with tetraploid embryos resulting in totally ES derived offspring; and 3) cloning by nuclear transfer. Homologous recombination may occur when using ES cells or when using the method of nuclear transfer.

The fertilised oocytes are centrifuged, for example, for eight minutes at 15,000 g to visualise the pronuclei for injection and then cultured from the zygote to morula or blastocyst stage in oviduct tissue-conditioned medium. This medium is prepared by using luminal tissues scraped from oviducts and diluted in culture medium. The zygotes must be placed in the culture medium within two hours following microinjection.

Oestrous is then synchronized in the intended recipient mammals, such as cattle, by administering coprostanol. Oestrous is produced within two days and the embryos are transferred to the recipients 5-7 days after oestrous. Successful transfer can be evaluated in the offspring by Southern blot.

Alternatively, the desired constructs can be introduced into embryonic stem cells (ES cells) and the cells cultured to ensure modification by the transgene. The modified cells are then injected into the blastula embryonic stage and the blastulas replaced into pseudopregnant hosts. The resulting offspring are chimeric with respect to the ES and host cells, and nonchimeric strains which exclusively comprise the ES progeny can be obtained using conventional cross-breeding. This technique is described, for example, in WO91/10741.

Alternative methods for delivery and stable integration of transposons and/or genes encoding transposases into the genome of host animals include the use of viral vectors, such as retroviral vectors, adenoviral vectors, baculoviral vectors and herpesviral vectors. Such techniques have moreover been described in the art, for example by Zhang et al. (Nucl. Ac. Res., 1998, 26:3687-3693).

Suitable viral vectors may be retroviral vectors, and may be derived from or may be derivable from any suitable retrovirus. A large number of different retroviruses have been identified. Examples include: murine leukaemia virus (MLV), human immunodeficiency virus (HIV), simian immunodeficiency virus, human T-cell leukaemia virus (HTLV), Equine infectious anaemia virus (EIAV), mouse mammary tumour virus (MMTV), Rous sarcoma virus (RSV), Fujinami sarcoma virus (FuSV), Moloney murine leukaemia virus (Mo-MLV), FBR murine osteosarcoma virus (FBR MSV), Moloney murine sarcoma virus (Mo-MSV), Abelson murine leukaemia virus (A-MLV), Avian myelocytomatosis virus-29 (MC29), and Avian erythroblastosis virus (AEV). A detailed list of retroviruses may be found in Coffin et al., 1997, "retroviruses", Cold Spring Harbour Laboratory Press Eds: J M Coffin, S M Hughes, H E Varmus pp 758-763.

Details on the genomic structure of some retroviruses may be found in the art. By way of example, details on HIV and Mo-MLV may be found from the NCBI GenBank (Genome Accession Nos. AF033819 and AF033811, respectively).

Retroviruses may be broadly divided into two categories: namely, "simple" and "complex". Retroviruses may even be further divided into seven groups. Five of these groups represent retroviruses with oncogenic potential. The remaining two groups are the lentiviruses and the spumaviruses. A review of these retroviruses is presented in Coffin et al., 1997 (ibid).

Host range and tissue tropism varies between different retroviruses. In some cases, this specificity may restrict the transduction potential of a recombinant retroviral vector. For this reason, many gene therapy experiments have used MLV. A particular MLV that has an envelope protein called 4070A is known as an amphotropic virus, and this can also infect human cells because its envelope protein "docks" with a phosphate transport protein that is conserved between man and mouse. This transporter is ubiquitous and so these viruses are capable of infecting many cell types.

Replication-defective retroviral vectors are typically propagated, for example to prepare suitable titres of the retroviral vector for subsequent transduction, by using a combination of a packaging or helper cell line and the recombinant vector. That is to say, that the three packaging proteins can be provided in trans.

A "packaging cell line" contains one or more of the retroviral gag, pol and env genes. The packaging cell line produces the proteins required for packaging retroviral DNA but it cannot bring about encapsidation due to the lack of a psi region. The helper proteins can package a psi-positive recombinant vector to produce the recombinant virus stock. This virus stock can be used to transduce cells to introduce the vector into the genome of the target cells. A summary of the available packaging lines is presented in Coffin et al., 1997 (ibid).

The lentivirus group can be divided into "primate" and "non-primate". Examples of primate lentiviruses include human immunodeficiency virus (HIV), and simian immunodeficiency virus (SIV). The non-primate lentiviral group includes the prototype "slow virus" visna/maedi virus (VMV), as well as the related caprine arthritis-encephalitis virus (CAEV), equine infectious anaemia virus (EIAV) and the more recently described feline immunodeficiency virus (FIV) and bovine immunodeficiency virus (BIV). See, for example, Rovira et al., (2000) Blood 96:4111-4117; Reiser et al., (2000) J. Virol. 74:10589-99; Mulder, M. P et al. (1995), Hum Genet 96:133-141):10589; Lai et al., Proc Natl Acad Sci USA (2000) 97:11297-302; Southern, E. M. (1975), J. Mol. Biol 98; 503-517; and Saulnier et al., (2000) J Gene Med 2:317-25.

A distinction between the lentivirus family and other types of retroviruses is that lentiviruses have the capability to infect both dividing and non-dividing cells. In contrast, other retroviruses—such as MLV—are unable to infect non-dividing cells such as those that make up, for example, muscle, brain, lung and liver tissue.

A number of vectors have been developed based on various members of the lentivirus sub-family of the retroviridae and a number of these are the subject of patent applications (WO-A-98/18815; WO-A-97/12622). Preferred lentiviral vectors are based on HIV, SIV or EIAV. The simplest vectors constructed from HIV-1 have the complete HIV genome except for a deletion of part of the env coding region or replacement of the nef coding region. Notably these vectors express gag/pol and all of the accessory genes and hence require only an envelope to produce infectious virus particles. Of the accessory genes vif, vpr, vpu and nef are non-essential.

One preferred general format for HIV-based lentiviral vectors is, HIV 5'LTR and leader, some gag coding region sequences (to supply packaging functions), a reporter cassette, the rev response element (RRE) and the 3'LTR. In these vectors gag/pol, accessory gene products and envelope functions are supplied either from a single plasmid or from two or more co-transfected plasmids, or by co-infection of vector containing cells with HIV.

The adenoviral vector system is also useful according to the methods of the invention. The adenovirus is a double-stranded, linear DNA virus that does not go through an RNA intermediate. There are over 50 different human serotypes of adenovirus divided into 6 subgroups based on the genetic sequence homology all of which exhibit comparable genetic organisation. Human adenovirus group C serotypes 2 and 5 (with 95% sequence homology) are most commonly used in adenoviral vector systems and are normally associated with upper respiratory tract infections in the young.

Adenoviruses/adenoviral vectors which may be used in the invention may be of human or animal origin. As regards the adenoviruses of human origin, preferred adenoviruses are those classified in group C, in particular the adenoviruses of type 2 (Ad2), 5 (Ad5), 7 (Ad7) or 12 (Ad12). Among the various adenoviruses of animal origin, canine adenovirus, mouse adenovirus or an avian adenovirus such as CELO virus (Cotton et al., 1993, J Virol 67:3777-3785) maybe used.

HSV vectors may be derived from, for example, HSV1 or HSV2 strains, or derivatives thereof. Attenuated strains may be used for example strain 1716 (MacLean et al., 1991, J Gen Virol 72: 632-639), strains R3616 and R4009 (Chou and Roizman, 1992, PNAS 89:3266-3270) and R930 (Chou et al., 1994, J. Virol 68: 8304-8311) all of which have mutations in ICP34.5, and d27-1 (Rice and Knipe, 1990, J. Virol 64:1704-1715) which has a deletion in ICP27. Alternatively strains deleted for ICP4, ICP0, ICP22, ICP6, ICP47, vhs or gH, with an inactivating mutation in VMW65, or with any combination of the above may also be used to produce HSV strains of the invention.

The terminology used in describing the various HSV genes is as found in Coffin and Latchman, 1996. Herpes simplex virus-based vectors. In: Latchman DS (ed). Genetic manipulation of the nervous system. Academic Press: London, pp 99-114.

Baculovirus vectors may moreover be employed in the invention. The baculovirus *Autographa californica* multiple nuclear polyhedrosis virus (AcMNPV) is a DNA virus which can replicate only in cells of certain lepidopteran insects and has been used widely for expression of recombinant proteins in insect cells. Baculoviruses such as AcMNPV have been used recently for introducing heterologous DNA with high efficiency in a variety of mammalian cells, such as a hepatoma cell line and primary liver cells, and endothelial cells (Boyce F M, Bucher N L (1996) *Baculovirus-mediated gene transfer into mammalian cells*. Proc Natl Acad Sci USA 93, 2348-52; Airenne K J, Hiltunen M O, Turunen M P, Turunen A M, Laitinen O H, Kulomaa M S, Yla-Herttuala S (2000) *Baculovirus-mediated periadventitial gene transfer to rabbit carotid artery*. Gene Ther 7, 1499-1504). Moreover, baculovirus vectors for gene transfer, methods for introducing heterologous DNA into their genome and procedures for recombinant virus production in insect cell cultures are available commercially; furthermore, baculoviruses cannot normally replicate in mammalian cells, so there is no need to engineer them for this use.

Construction of vectors for use in methods of the invention may employ conventional ligation techniques. Isolated viral vectors, plasmids or DNA fragments are cleaved, tailored, and religated in the form desired to generate the plasmids required. If desired, analysis to confirm correct sequences in the constructed vectors is performed in a known fashion. Transposon presence and/or mobilisation may be measured in a cell directly, for example, by conventional Southern blotting, dot blotting, PCR or in situ hybridisation, using an appropriately labelled probe which may be based on a sequence present in the transposon. Those skilled in the art will readily envisage how these methods may be modified, if desired. Vectors useful in the present invention are advantageously provided with marker genes to facilitate transposon identification and localisation as described above.

Uses of the Invention

The methods of the present invention enables the generation of transgenic embryos and organisms comprising one or more clonal populations of cells homogeneous for one or more individual mutations. Thus, transgenic embryos and animals can be produced in which a cluster of cells, a tissue or tissues, or an organ or group of organs each share the same genetic modification. The presence of the same genetic modification in a number of cells, tissues or organs enables convenient phenotypic and genotypic analysis of the modification and moreover enables the comparison of the effects of a particular gene modification to be compared with corresponding wild-type genes or indeed other gene modifications in the same type of cell, tissue or organ within the same organism.

The invention may further be used to monitor gene expression patterns of modified genes during embryo development and in adult cells and tissues.

Transposons, and sites from which transposons have been excised, may be identified by sequence analysis. For example, Minos typically integrates at a TA base pair, and on excision leaves behind a footprint, consisting of duplication of the target TA sequence, flanking the four terminal nucleotides of the transposon. The presence of the sequence of Minos, its footprint, or related sequences, may be detected by techniques such as sequencing, PCR or hybridisation.

Inserted transposons may be identified by similar techniques, for example using PCR primers complementary to the terminal repeat sequences.

The invention allows functional mapping of a genome by permitting precise gene modulation at predetermined stages of development and subsequent detection using transposons. Thus, the invention provides for efficient intracellular transposon mobilisation and insertion into the cell genome of one or more cells or tissues of an organism, providing exon trapping functionality in cells of transgenic organisms at early stages of development. The induction of transposon mobilisation at such stages of embryonic development enables the generation of clusters of cells or tissues which are homogeneous for a transposed gene. This may therefore enable rapid and efficient detection of a change in phenotype and/or identification of the modified gene.

Figure 12:
FIG. 12 illustrates a trap construct for transgenic mice and/or cloning into retroviral plasmid.
Figure 13:
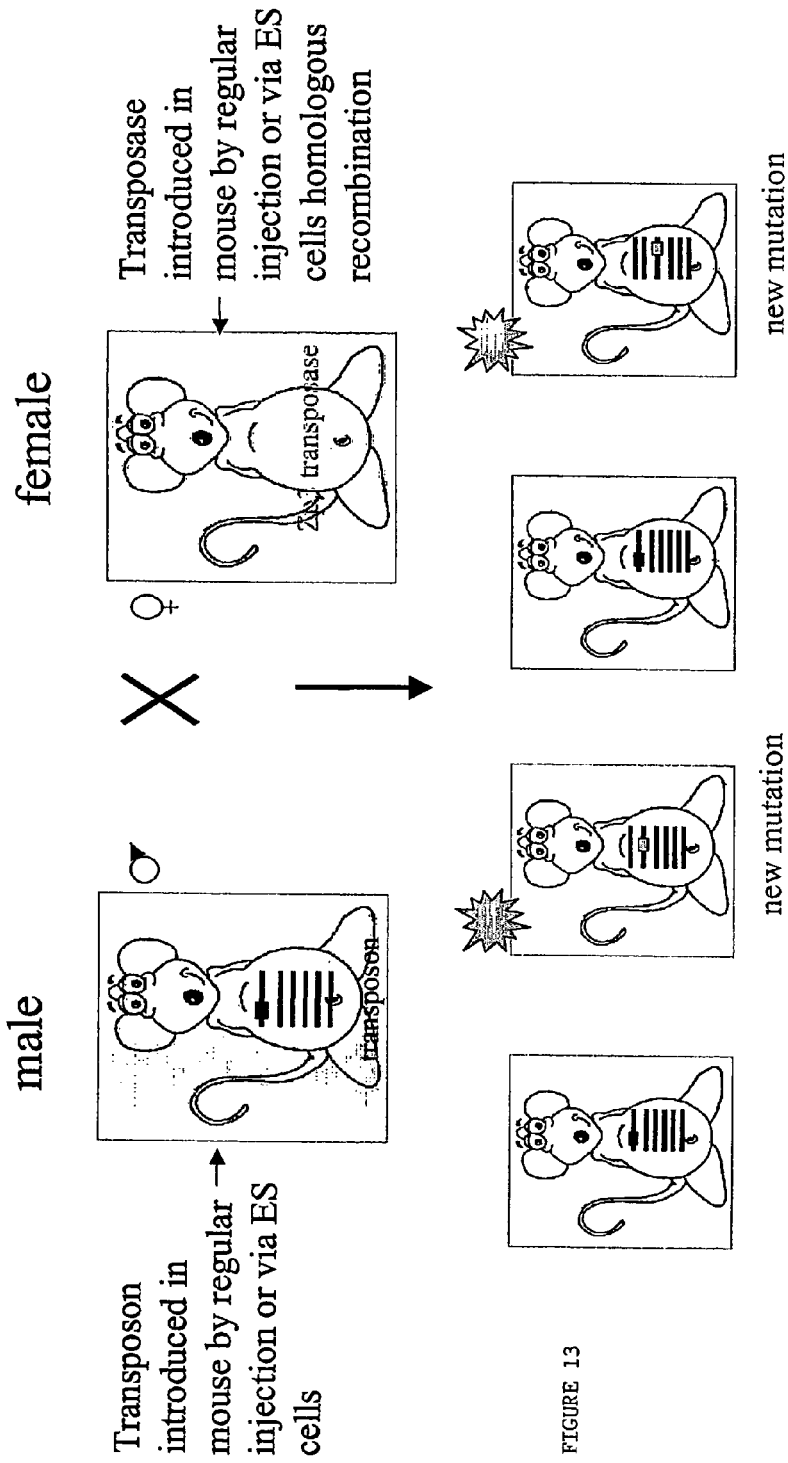
FIG. 13 is a diagram showing in vivo transposition occurring in the egg or early embryo. Double positive females are obtained by crossing a transposase-positive female with a transposon-positive male or by crossing a transposase-positive male with a transposon-positive female.
Figure 14:
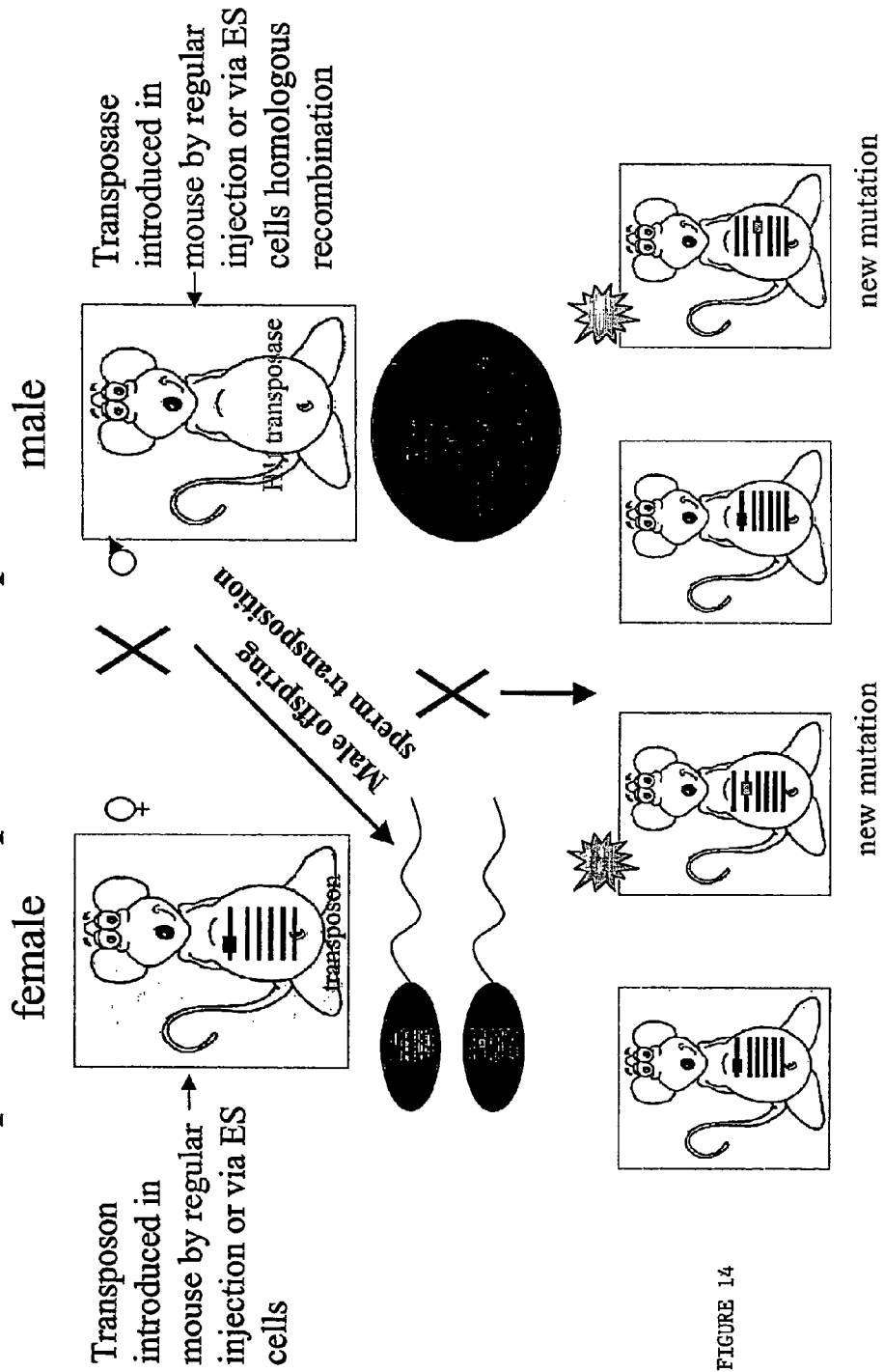
FIG. 14 is a diagram showing in vivo transposition occurring in the sperm. Double positive males are obtained by crossing a transposase-positive female with a transposon-positive male or by crossing a transposase-positive male with a transposon-positive female.
Figure 15:
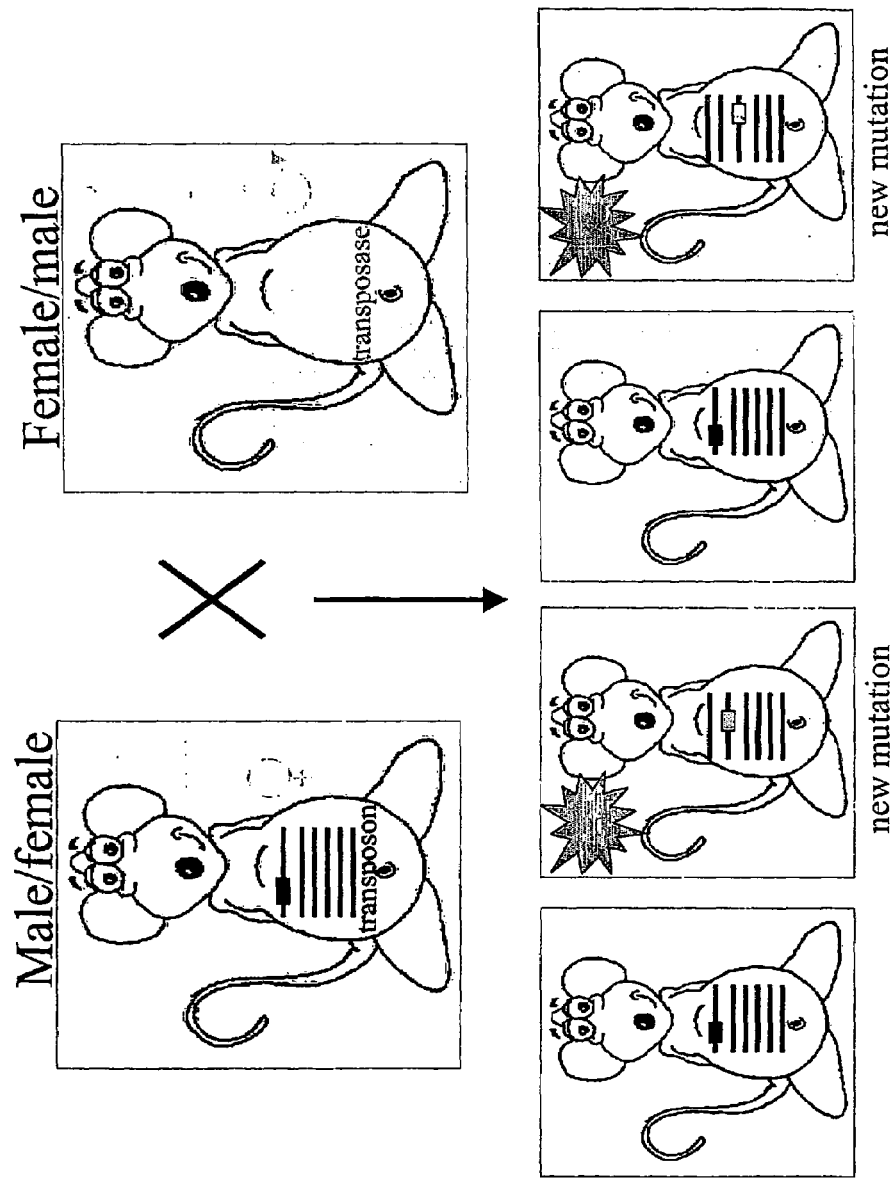
FIG. 15 is a diagram showing in vivo transposition with the male or female contributing the transposon, and the male or female contributing the transposase. Transposition takes place in the fertilised egg or embryo or the sperm.

An example of a suitable trap construct is given in FIG. 12.

The invention, in an advantageous embodiment, allows genes to be marked for functional genetic analysis in a group of cells or tissues, or knocked out, by transposon insertion and then specifically identified through the transposon "tag" without requiring costly and time-consuming genetic analyses, and frequently without significant amounts of sequencing.

A further embodiment of the invention provides for the generation of libraries of transgenic organisms, such as transgenic mice. Target genes may be identified phenotypically according to the phenotype of one or more cells, tissues or organs, and identified genetically by determination of the transposon insertion site. Inducible expression systems, as described above, may be used to regulate the switch between partial and antisense-induced complete knockout of a gene. Somatic cells carrying transposon insertions can be immortalized, for example by deriving immortal cell lines by standard methodologies, or by generating transgenic animal lines by nuclear implantation methodologies.

Such libraries can be used for phenotypic analysis and identification of gene associations. The present methods allow advantages over the current methods.

In inherited diseases such as the haemoglobinopathies, haemophilia, cystic fibrosis, and muscular dystrophy, well defined mutations in single genes or their regulatory elements result in inappropriate gene expression with clinical consequences which profoundly effect the life style and life expectancy of affected individuals.

However in other diseases particularly those related to aging, such as the dementias; psychiatric disorders such as schizophrenia and manic depression; bone and joint related inflammatory conditions; obesity, insulin resistance, type 2 diabetes and related vascular and cardiovascular conditions; the genetic component is more complex and still poorly understood (see Lander and Schork, Science (1994) 265, 2037-2048).

Where multiple mutations in different targets determine factors such as the time of disease onset (eg post menopausal insulin resistance) and severity of the disease state (eg predisposition to vascular disease and stroke) strategies based on random alkylation of inbreed mouse strains, and transgenic mice developed from single gene deletions in vast ES cell libraries seem destined to fail.

The present invention provides a more attractive strategy through the rapid generation of randomly "tagged" mouse strains starting with a background known to be prone to a disease state, and therefore likely to have existing mutations in interrelated disease causing genes. The background can be selected by using founder cell lines carrying multiple "dormant" transposons at known integration sites. Regulatable transposase activity will allow the rapid generation of mouse libraries in different genetic backgrounds reflecting differing models of disease.

For example it has been shown that the mutations in the insulin receptor cause mild to severe hyperinsulinemia dependent on the mouse genetic background (see Kido (2000) Diabetes 49, 589-596) indicating the involvement of other genes in the predisposition to insulin resistance. Thus generation of a tagged mouse library using in vivo gene transposition technology in the "mild phenotype" mouse background should lead to selection of animals with a more severe phenotype. Sequence analysis of DNA flanking new transposition events will then identify new candidate disease causing genes which contribute to the onset of the severe phenotype.

Candidate disease genes can then become the focus of further studies to determine their precise role in animal models, and validation of a disease related role in man.

Target validation in man will utilise existing clinical and genetic databases, containing DNA and clinical information on relevant patient and control groups.

Phenotypic analysis of the transgenic organisms created can be through simple and rapid measurements including changes in a metabolite, protein (e.g. insulin), lipid or carbohydrate (e.g. when measuring glucose tolerance) present in urine, blood, spinal fluid or tissue.

Other phenotypic characteristics can be analysed by measuring behavioural patterns or responses to external stimuli by using tests such as light, sound, memory and stress tests.

Other measurable phenotypic characteristics include growth and ageing parameters, tumour growth, obesity and so forth which can be measured by assessing, for example, weight, fat content and growth rate. Furthermore changes in other measurable features such as blood pressure, heart rate, lung function and so forth can be assessed.

Advantageously, the transposon technology of the present invention allows the production of libraries of transgenic animals without the requirement for extensive storage. Previous methods of generating transgenic animals involve methods such as chemical mutagenesis in which mutations are generated. These methods involve multiple mutations per animal (e.g. mouse). The animals, once generated are analysed phenotypically and then need to be archived/stored for use in the future. The present invention allows the generation of starter cell lines or starter transgenic organisms having different transposons inserted into the genome. These cell lines or organisms can then be used by breeding with transgenic animals carrying a transposase to generate a new library.

In another embodiment, the methods of the invention may be used to generate libraries of ES cells with different transposon insertions distributed throughout the genome. These can be sequenced and characterised. The ES cells can conveniently be stored for future use.

In an alternative embodiment, the methods of the invention may be used to "mark" genes whose expression is modulated by external stimuli. Thus, an embryo, organism, or tissue or cell derived from either, which has been exposed to transposon mobilisation with a marked transposon is subjected to treatment with an external stimulus, such as a candidate drug or other test agent, and modulation of the expression of the marker observed. Cells in which the marker is over or under-expressed are likely to have the transposon inserted in or near a gene which is upregulated or downregulated in response to the stimulus. The invention may thus be used to provide in vivo enhancer trap and exon trap functions, by inserting transposons which comprise marker genes which are modulated in their expression levels by the proximity with enhancers or exons.

This approach is useful for the study of gene modulation by drugs in drug discovery approaches, toxicology studies and the like. Moreover, it is applicable to study of gene modulation in response to natural stimuli, such as hormones, cytokines and growth factors, and the identification of novel targets for molecular intervention, including targets for disease therapy in humans, plants or animals, development of insecticides, herbicides, antifungal agents and antibacterial agents.

The invention is further described, for the purpose of illustration, in the following examples.

EXAMPLES

A: Activation of Minos In Vivo Using Doxycycline

Example 1

Generation of Transposon Carrying Mice and Transposase Carrying Mice

Two transgenic mouse lines are generated. The transposon-carrying line (line MCG) contains a tandem array of a fragment containing a Minos transposon containing the GFP gene under the control of the cytomegalovirus promoter. The transposon is engineered such that almost all sequence internal to the inverted repeats is replaced by the CMV/GFP cassette. Not containing the transposase-encoding gene, this transposon is non-autonomous, and can only be mobilized when a source of transposase is present. The second transgenic mouse line contains the Minos transposase gene expressed under the control of the inducible promoter.

Figure 5:
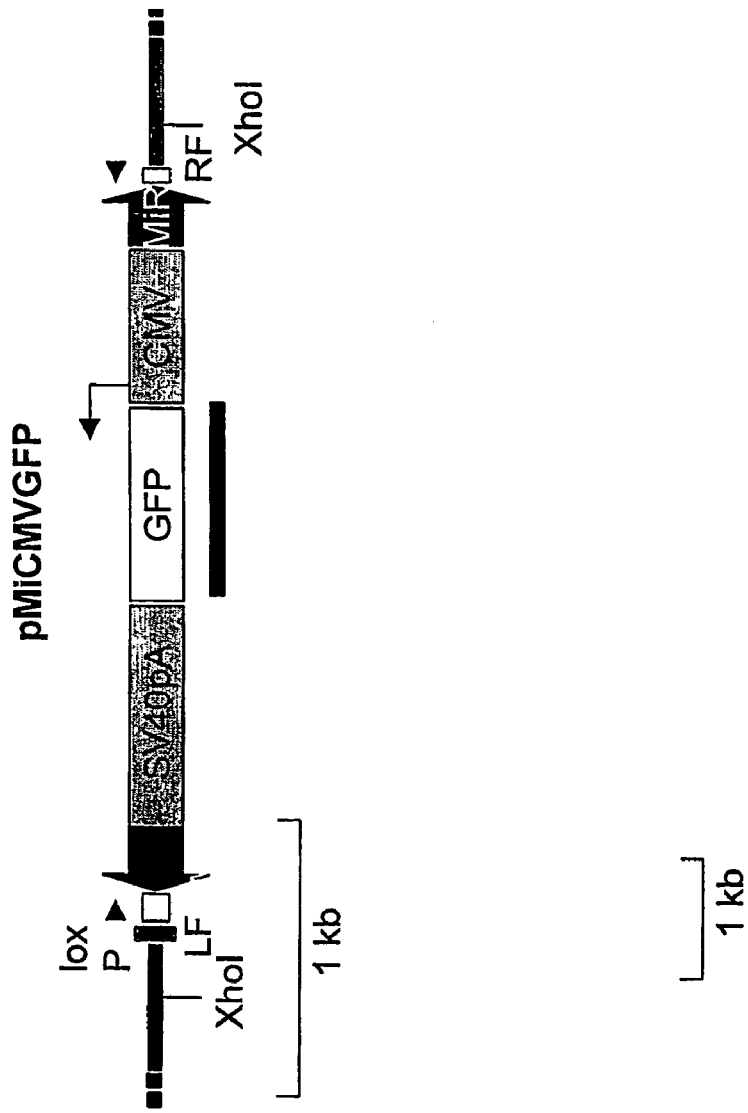
FIG. 5 shows the Minos derived vector pMiCMVGFP. Minos inverted terminal repeats are shown as thick black arrows. White blocks outside these arrows indicate the sequences flanking the original Minos element in the *D. hydei* genome. Arrowheads indicate the positions of primers used to detect Minos excisions. Small arrows indicate the direction of transcription of the GFP and transposase genes. Black bars represent fragments used as probes.

Transposon MiCMVGFP was constructed as follows: The plasmid pMILRTetR (Klinakis et al. (2000) *Ins. Mol. Biol.* 9, 269-275 (2000b)) was cut with BamHI and religated to remove the tetracycline resistance gene between the Minos ends, resulting in plasmid pMILRΔBamH1. An Asp718/SacI fragment from pMILRΔBam Hi, containing the Minos inverted repeats and original flanking sequences from *D. hydei*, was cloned into plasmid pPolyIII-I-lox (created by insertion of the loxP oligo:

```
ATAACTTCGTATAGCATACATTATACGAAGTTAT (SEQ ID NO: 1)
``` into the Asp71 8 site of the vector pPolyIII-I (accession No. M18131)), resulting in plasmid ppolyMILRΔBamH. The final construct (pMiCMVGFP, FIG. 5) used for the generation of transgenic mice, was created by inserting into the Spe I site of ppolyMILRΔBamH1 the 2.2 kb SpeI fragment from plasmid pBluescriptGFP, containing a humanised GFP gene (from Clontech plasmid pHGFP-S65T) driven by the CMV promoter and followed by the SV40 intervening sequence and polyadenylation signal.

The transposon-carrying MCG line was constructed by microinjecting the 3.2 kb XhoI fragment from the pMiCMVGFP plasmid into FVB X FVB fertilized oocytes. Transgenic animals were identified by Southern blotting of DNA from tail biopsies, using GFP DNA as a probe.

The transposase-expressing line is generated via methods known in the art and described herein, including but not limited to microinjection of fertilized eggs; transfection or infection of ES cells followed by injection of ES cells into blastocysts or fusion of ES cells with tetraploid embryos, or alternatively, cloning by nuclear transfer. The transposase gene may be introduced into embryonic stem cells via standard transfection or homologous recombination ES cell technology. The ES cells are injected into blastocysts to obtain transgenic animals via standard procedures (Manipulating the mouse embryo, Hogan et al., Cold Spring Harbor Press, 1994). Two constructs are used: First, a construct containing the rtTA gene under a constitutive promoter expressed in the target cells. The construct used is the pTet-On plasmid (Clontech) which contains the gene encoding the rtTA activator under control of the Cytomegalovirus immediate early (CMV) promoter. The rtTA transcriptional activator encoded by this construct is active only in the presence of Doxycycline. The second construct contains the Minos transposase gene under control of the tetracycline-response element, or TRE. The TRE consists of seven direct repeats of a 42-bp sequence containing the tet operator (tetO), and is located just upstream of the minimal CMV promoter, which lacks the enhancer elements normally associated with the CMV immediate early promoter. Because these enhancer elements are missing, there is no "leaky" expression of transposase from the TRE in the absence of binding by rtTA. The second construct used is the pTRE2 plasmid (Clontech) in the multiple cloning site (MCS) of which is inserted the gene encoding Minos transposase. In cells stably transformed with the two constructs, rtTA is expressed but does not activate transcription of Minos transposase unless Doxycycline is administered.

Transgenic animals are identified by Southern blotting of DNA from tail biopsies, using a transposase cDNA fragment as a probe.

Example 2

Activation of Minos In Vivo

A transgenic mouse of the transposon-carrying MCG line is crossed with a transgenic mouse of the transposase carrying line. Mobilisation of transposons in resulting embryos comprising within their genomes both the transposon and the gene encoding the transposase will only occur in the presence of Doxycycline. Doxycycline is administered to the embryos in the water of the maternal organism. Doxycycline is only administered for a limited amount of time (one day-day 2 of gestation) in order to restrict the potential number of transposition events.

On birth, the transgenic offspring developed from the embryos are isolated and various cells and tissues are used for genotyping.

Example 3

Detection of Transposition

A PCR assay for transposon excision is used to detect active transposition by Minos transposase in the mouse tissues, using primers that hybridise to the non-mobile *Drosophila hydei* sequences which flank the Minos transposon in the constructs (Klinakis et al. (2000) *Ins. Mol. Biol.* 9, 269-275). In *Drosophila* cells, transposase-mediated excision of Minos is followed by repair of the chromatid which usually leaves a characteristic 6-base pair footprint (Arca et al. (1997)

Genetics 145, 267-279). With the specific pair of primers used in the PCR assay this creates a diagnostic 167 bp PCR fragment (Catteruccia F. et al. (2000) *Proc. Natl. Acad. Sci. USA* 97, 2157-2162). Genomic DNA from different tissues is isolated with the DNeasy Tissue-Kit (QIAGEN) according to the manufacturers instructions. PCR reactions are performed using primers

11DML:

```
(5'AAGTGTAAGTGCTTGAAATGC-3' (SEQ ID NO: 2))
``` and GOUM67:

```
(5'-GCATCAAATTGAGTTTTGCTC-3' (SEQ ID NO: 3)).
```

PCR conditions are as follows: 10 mM Tris-HCl (pH 8.8), 50 mM KCl, 1.5 ruM $MgCl_2$, 0.001% gelatin; 1.2 units Taq 2000™ DNA Polymerase (STRATAGENE), 200 g template DNA and 10 pmol of each primer per 25 µl reaction. 43 or 60 cycles of 30" at 94° C., 30" at 59° C. and 30" at 72° C. were performed. PCR products are cloned into the PCRII TA cloning vector (Invitrogen) and are sequenced using the T7 primer.

The diagnostic band is present in certain tissues of the transgenic offspring. The identity of the fragment is confirmed by Southern blot analysis using a labelled DNA probe specific for the amplified sequence (data not shown). Clusters of cells are shown to be homogeneous for the same transposed gene.

B: Activation of Minos In Vivo Using Transposase Under the Control of the ZP3 Promoter

Example 4

In this example, it is demonstrated that, by placing expression of the gene encoding the transposase under the control of a gene regulatory signal produced at a particular stage of development, transposition can be induced at that stage of embryo development. In this example, the gene encoding the transposase was placed under the control of the ZP3 promoter, and so the transposase was only expressed in growing oocytes during a 2-to-3-week period of oogenesis. The Minos transposase expressed in growing oocytes catalysed the excision of a modified, non autonomous Minos transposon and promoted its re-integration into new sites of the genome.

FIG. 11 shows alternative constructs (constructs for knock-in and for regular transgenesis) in which the transposase is inserted in the endogenous sperm specific H1t gene for transposition in sperm. Alternative constructs are made for egg specific expression or ubiquitous expression by replacing H1t sequences with equivalent sequences flanking the start of the Zp3 (egg specifically expressed) or hnRNP (ubiquitously expressed) gene. The invention encompasses any egg specific, sperm specific or endogenous regulatory sequence known in the art.

C: Mammalian Codon Usage in Minos Sequence

Example 5

Improving Transposase

One of the ways to improve the efficiency of the fly transposase in mammalian cells or animals is to increase its concentration as a result of a more efficient translation from mRNA by replacing the fly codon usage to mammalian codon usage. To this end we replaced the coding sequence of the fly Minos transposase with the sequence (SEQ ID NO: 4):

SEQ New: 1026 bp;

Composition 321 A; 235 C; 261 G; 209 T; 0 OTHER

Percentage: 31% A; 23% C; 25% G; 20% T; 0% OTHER

Molecular Weight (kDa): ssDNA: 317.79 dsDNA: 632.5

Origin

```
  1 ATGGTGCGCG GTAAGCCTAT CTCTAAGGAG ATCAGAGTAC TGATCAGGGA CTATTTTAAG
 61 TCTGGGAAGA CACTCACTGA GATAAGCAAG CAGTTAAACT TGCCTAAGAG CTCTGTGCAT
121 GGGGTGATAC AGATTTTCAA GAAAAATGGG AACATTGAGA ATAACATCGC GAATAGAGGC
181 CGAACATCCG CAATAACCCC CCGCGACAAG AGACAGCTGG CCAAAATTGT GAAGGCTGAC
241 CGCCGCCAAT CCCTGAGAAA CTTGGCTTCC AAGTGGTCGC AGACCATTGG CAAGACTGTC
301 AAGCGGGAGT GGACCCGGCA GCAATTAAAG AGTATTGGCT ACGGTTTTTA TAAGGCCAAG
361 GAAAAACCCC TGCTTACGCT TCGGCAAAAA AAGAAGCGTC TGCAATGGGC TCGGGAAGG
421 ATGTCTTGGA CTCAAAGGCA GTGGGATACC ATCATCTTCA GCGATGAGGC TAAATTTGAT
481 GTGAGTGTCG GCGACACGAG AAAGCGCGTC ATCCGTAAGA GGTCCGAGAC ATACCATAAG
541 GACTGCCTGA AAAGAACAAC CAAGTTTCCT GCAAGCACTA TGGTATGGGG ATGTATGTCT
601 GCCAAAGGAC TCGGAAAGCT TCACTTCATC GAAGGGACCG TTAATGCCGA AAAATACATT
661 AACATTCTCC AGGATAGTTT GCTGCCCTCA ATACCAAAAC TATCCGATTG TGGTGAATTC
721 ACTTTTCAGC AGGACGGAGC ATCATCGCAC ACCGCCAAGC GGACCAAAAA CTGGCTGCAG
781 TACAATCAGA TGGAGGTGCT CGATTGGCCC TCAAATAGTC CGGATCTAAG CCCAATCGAA
841 AATATCTGGT GGCTAATGAA AAACCAGCTG CGAAACGAGC CACAGAGGAA CATTTCCGAC
```

```
 901 TTGAAAATCA AGCTGCAAGA GATGTGGGAC TCAATCTCTC AGGAGCACTG CAAAAACCTG

961 CTCAGCAGCA TGCCTAAACG AGTGAAATGC GTGATGCAGG CCAAGGGCGA CGTTACACAG

1021 TTCTGA
```

This sequence corresponds to the normal mammalian codon usage and results in a protein sequence after translation that is identical to the fly transposase protein sequence. The gene (cDNA) was synthesized from overlapping oligonucleotides in three parts (4 for part A and B and 6 for part C, see below) (upper, sense strand, lower antisense strand overlapping oligonucleotides are shown in bold). Each part was filled in by polymerase, ligated and then amplified by PCR using the outer 5' oligonucleotides of each DNA strand, and cloned. The three parts were subsequently put together in one cDNA by standard ligation and cloning:

part A plus the Kozak sequence preceding the start codon (Top 5); Bottom Strand: (SEQ ID NO: 26).

```
            AatII    NcoI
    -15 CCCCGACGTCCCACCATGGTGCGCG GTAAGCCTAT CTCTAAGGAG ATCAGAGTAC TGATCAGGGA CTATTTTAAG

TACCACGCGC CATTCGGATA GAGATTCCTC TAGTCTCATG ACTAGTCCCT GATAAAATTC

61                  TCTGGGAAGA CACTCACTGA GATAAGCAAG CAGTTAAACT TGCCTAAGAG CTCTGTGCAT

AGACCCTTCT GTGAGTGACT CTATTCGTTC GTCAATTTGA ACGGATTCTC GAGACACGTA

121     GGGGTGATAC AGATTTTCAA GAAAAATGGG AACATTGAGA ATAACATCGC GAATAGAGGC

CCCCACTATG TCTAAAAGTT CTTTTTACCC TTGTAACTCT TATTGTAGCG CTTATCTCCG

181     CGAACATCCG CAATAACCCC CCGCGACAAG AGACAGCTGG CCAAAATTGT GAAGGCTGAC

GCTTGTAGGC GTTATTGGGG GGCGCTGTTC TCTGTCGACC GGTTTTAACA CTTCCGACTG

241     CGCCGCCAAT CCCTGAGAAA CTTGGCTTCC AAGTGGTCGC AGACAATTGG CAAGACTGTC

GCGGCGGTTA GGGACTCTTT GAACCGAAGG TTCACCAGCG TCTGTTAACC TGATCAGGGG
                                                            MfeI       SpeI
```

Linker B: Top Strand: (SEQ ID NO: 6): Bottom Strand (SEQ ID NO: 27)

```
                                                            MfeI
                                                       GGGGCAATTGG CAAGACTGTC

GCGGCGGTTA GGGACTCTTT GAACCGAAGG TTCACCAGCG TCTGTTAACC GTTCTGACAG

301 AAGCGGGAGT GGACCCGGCA GCAATTAAAG AGTATTGGCT ACGGTTTTTA TAAGGCCAAG

TTCGCCCTCA CCTGGGCCGT CGTTAATTTC TCATAACCGA TGCCAAAAAT ATTCCGGTTC

361 GAAAAACCCC TGCTTACGCT TCGGCAAAAA AAGAAGCGTC TGCAATGGGC TCGGGAAAGG

CTTTTTGGGG ACGAATGCGA AGCCGTTTTT TTCTTCGCAG ACGTTACCCG AGCCCTTTCC

421 ATGTCTTGGA CTCAAAGGCA GTGGGATACC ATCATCTTCA GCGATGAGGC TAAATTTGAT

TACAGAACCT GAGTTTCCGT CACCCTATGG TAGTAGAAGT CGCTACTCCG ATTTAAACTA

481 GTGAGTGTCG GCGACACGAG AAAACGCGTC ATCCGTAAGA GGTCCGAGAC ATACCATAAG

CACTCACAGC CGCTGTGCTC TTTTGCGCAG TAGGCATTCT CCAGGCTCTG TATGGTATTC

541 GACTGCCTGA AAAGAACAAC CAAGTTTCCT GCAAGCACTA TGGTATGGGG ATGTATGTCT

CTGACGGACT TTTCTTGTTG GTTCAAAGGA CGTTCGTGAT ACCATACCCC TACATACAGA

601 GCCAAAGGAC TCGGAAAGCT TCACTTCATC GAAGGGACCG TTAATGCCGA AAAATACATT

CGGTTTCCTG AGCCTTTCGA ACCCCTACGTACCCC
                HindIII            NsiI
```

Linker C: Top Strand: (SEQ ID NO: 7): Bottom Strand (SEQ ID NO: 28)

```
              HindIII
 601          CCCCAAGCT TCACTTCATC GAAGGGACCG TTAATGCCGA AAAATACATT

TTCGA     AGTGAAGTAG CTTCCCTGGC AATTACGGCT TTTTATGTAA

661 AACATTCTCC AGGATAGTTT GCTGCCCTCA ATACCAAAAC TATCCGATTG TGGTGAATTC

TTGTAAGAGG TCCTATCAAA CGACGGGAGT TATGGTTTTG ATAGGCTAAC ACCACTTAAG

721 ACTTTTCAGC AGGACGGAGC ATCATCGCAC ACCGCCAAGC GGACCAAAAA CTGGCTGCAG

TGAAAAGTCG TCCTGCCTCG TAGTAGCGTG TGGCGGTTCG CCTGGTTTTT GACCGACGTC

781 TACAATCAGA TGGAGGTGCT CGATTGGCCC TCAAATAGTC CGGATCTAAG CCCAATCGAA

ATGTTAGTCT ACCTCCACGA GCTAACCGGG AGTTTATCAG GCCTAGATTC GGGTTAGCTT

841 AATATCTGGT GGCTAATGAA AAACCAGCTG CGAAACGAGC CACAGAGGAA CATTTCCGAC

TTATAGACCA CCGATTACTT TTTGGTCGAC GCTTTGCTCG GTGTCTCCTT GTAAAGGCTG

901 TTGAAAATCA AGCTGCAAGA GATGTGGGAC TCAATCTCTC AGGAGCACTG CAAAAACCTG

AACTTTTAGT TCGACGTTCT CTACACCCTG AGTTAGAGAG TCCTCGTGAC GTTTTTGGAC

961 CTCAGCAGCA TGCCTAAACG AGTGAAATGC GTGATGCAGG CCAAGGGCGA CGTTACACAG

GAGTCGTCGT ACGGATTTGC TCACTTTACG CACTACGTCC GGTTCCCGCT GCAATGTGTC

1021 TTCTGAGGAT CC

AAGACTCCTA GGCCCCGGGG AGATCTCCTA CGTAGGGG
             BamHI      XbaI      NsiI
```

Materials and Methods

Plasmid Construction

The construction of the modified Minos transposon pMiC-MVGFP (FIG. 5), which was used for the generation of transgenic mice, is described in Example 1. In short, a 2.2 kb fragment, containing a humanised GFP gene driven by a CMV promoter and followed by an intervening sequence and an SV40 poly A signal, was positioned between Minos inverted repeats. A lox P site was included in front of the left inverted repeat for the generation of single copy transgenic animals if needed.

The Minos transposase cDNA was cloned as a 1 kb ClaI/NotI fragment in the vector Pev3 (Clare Gooding, Biotechnology Dept, Zeneca, Macclesfield, UK; Pev3 is further described in Needham et al., Nucl. Acids Res., 20, 997-1003, 1992) A 3.8 kb ClaI/Asp718 fragment from the resulting plasmid (containing the Minos transposase cDNA followed by an intron and a polyadenylation signal from the human β globin gene) was cloned in pBluescript SK+ (Stratagene, La Jolla, Calif., USA) creating the plasmid pBlue/ILMi/3'β. A 6.5 kb blunt Asp718 fragment from plasmid ZP3/6.5Luc (Lira, S. et al (1990) Proc. Natl. Acad. Sci. USA 87, 7215-7219.) containing the 5'flanking region and promoter of the zona pellucida 3 (ZP3) gene was cloned into the EcoRV site of pBlue/ILMi/3'β, resulting in plasmid ZP3/ILMi (FIG. 6), which was used for the generation of transgenic mice expressing the transposase in developing eggs.

Generation of Transgenic Mice

To generate Minos transposase expressing lines, a 10.3 kb SmaI/Asp718 fragment was excised from pZP3/ILMi (FIG. 6), separated from plasmid sequences by gel electrophoresis (Sambrook, J et al Molecular Cloning. A Laboratory Manual. Cold Spring Harbor Laboratory Press, Cold Spring Harbor, N.Y. (1989)), purified and concentrated using an ELUTIP-d column (Schleicher & Schuell GmbH, Dassel, Germany) and injected into fertilised oocytes (FVBxFVB) at a concentration of 4 ng/μl. Injected eggs were transferred into pseudopregnant mice and transgenic offspring was identified by Southern blot analysis of tail DNA (Southern, E. M. (1975). J. Mol. Biol 98, 503-517).

The transposon carrying (MCG) line was generated as described above and in (Zagoraiou, L et al (2001) Proc. Natl. Acad. Sci. USA 98, 11474-11478).

RT-PCR

For RT-PCR analysis, total RNA was isolated from different organs of ZP3/ILMi transgenic mice using the Ultraspec RNA isolation system (Biotech Laboratories, Houston, Tex., USA). From 1 μg of total RNA, cDNA was synthesised in a 20 μl reaction using Reverse Transcriptase (Super RT; HT Biotechnology, Cambridge, UK) and oligo(dT) primer. PCR reactions were performed in a volume of 50 μl PCR buffer (Life Technologies, Paisley, UK) containing 1 μl of the cDNA from the RT reaction, 1.5 mM MgCl2, 100 ng of each primer, 0.2 mM dNTPs and 2.5 U Taq DNA polymerase (Pharmacia). A total number of 25 cycles were performed with denaturation at 94° C. for 45 seconds, annealing at 55° C. for 30 seconds and extension at 72° C. for 45 seconds. PCR products were visualised by electrophoresis on a 2% agarose gel. The Minos transposase specific primers Minos1: 5'-CAGCTTCGAAATGAGCCAC-3' (SEQ ID NO: 8) and beta EX: 5'-TGGACAGCAAGAAAGCGAG-3' (SEQ ID NO: 9) were used. Primers specific for murine hypoxanthine phosphoribosyltransferase (HPRT) were: 5'CACAGGACTAGAACAC-CTGC-3' (SEQ ID NO: 10) and 5'-GCTGGTGAAAAG-GACCTCT-3' (SEQ ID NO: 11).

Breeding Program

Transposon carrying (MCG) females were bred with ZP3/ILMi line 15 males. Double positive females obtained from these crosses were bred with wild type (WT) males and their offspring analysed by Southern blot analysis for possible transposition events. Genomic DNA was digested either with EcoRV or BglII, separated on a 0.7 or 1% agarose gel (Sigma, Steinheim, Germany), blotted onto a nylon membrane (Hybond-N+, Amersham Pharmacia, Buckinghamshire England) and probed with $^{32}$P labelled 737 bp SacI/NotI GFP fragment from pMiCMVGFP.

DNA Fluorescent In Situ Hybridisation (FISH) Analysis

Mouse metaphase spreads were prepared according to routine procedures from peripheral white blood cells (Mulder, M. P et al. (1995). *Hum Genet* 96(2):133-141). The 737-bp SacI/NotI GFP fragment from the pMiCMVGFP construct was used as a probe. The probe was either labelled with biotin (Boehringer Mannheim) and immunochemically detected directly with FITC or a tyramide based step was included to improve signal detection (Raap, A. K. et al (1995) *Human Molecular Genetics* 4, 529-534). The DNA was counterstained with DAPI.

Cloning of the Insertion Sites

Mouse DNA from animals with a new Minos insertion site was cut with EcoRV or BglII and resolved in a 0.7% agarose gel. The gel regions containing transposition events were cut out and the DNA was isolated. Depending on the fragment size, inverse PCR was performed either directly on self-ligated fragments using Minos primers Imio1 (5' AAGAGAATAAAATTCTCTTTGAGACG 3' (SEQ ID NO: 12)) for the first PCR and IMio2 (5' GATAATATAGTGTGTTAAACATTGCGC 3' (SEQ ID NO: 13)) for the nested PCR (Klinakis, A. G., Zagoraiou, L., Vassilatis, D. K & Savakis, C. (2000) EMBO Reports 11, 416-421), or the obtained EcoRV or BglII fragments were further digested with AluI and then circularised. Inverse PCR was performed with Minos primers Imio1 and Imii1 (5' CAAAAATATGAGTAATTTATTCAAACGG 3' (SEQ ID NO: 14)), followed by nested PCR 20 with primers IMio2 and IMii2 (5' GCTTAAGAGATAAGAAAAAAGTGACC 3' (SEQ ID NO: 15)) as previously described (Klinakis, A. G., Zagoraiou, L., Vassilatis, D. K & Savakis, C. (2000) EMBO Reports 11, 416-421). In this way, left and right flanks were amplified separately. The PCR fragments were either sequenced directly or after cloning into the pGEM T easy vector (Promega), or PCRII vector (Invitrogen). With the sequences obtained, a BLAST search was performed against the mouse genome sequences available at the time in the Celera (www.celera.com) database.

Results

Figure 7:
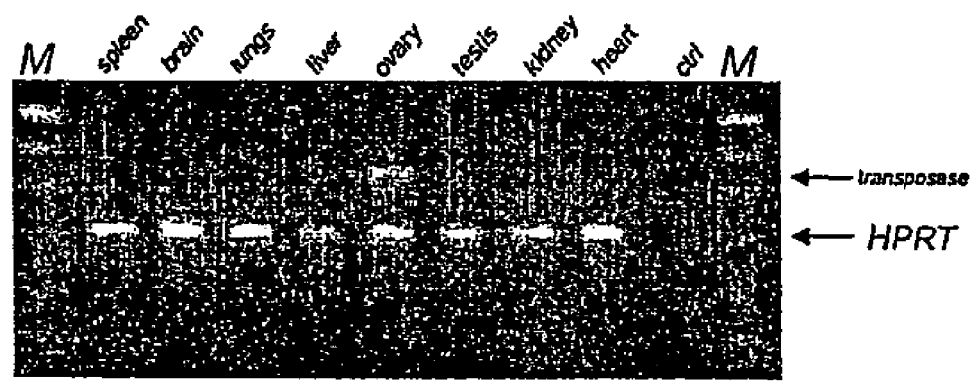
FIG. 7 illustrates detection of the Minos transposase transcription by RT-PCR analysis. The different tissues that were analysed are indicated. The murine hypoxantine phosphoribosyltransferase (HPRT) was used as an internal control. pUC 18 DNA MspI digested was used as a marker (M) and $H_2O$ in the negative control.

The transposon carrying transgenic mouse line (MCG) was generated. It contains 6 copies of Minos transposon MiCMVGFP (FIG. 5) integrated in mouse chromosome 14. The transposon is nonautonomous, i.e. it cannot transpose on its own, since it lacks the transposase gene. In parallel, two transposase expressing mouse lines were generated. These expressed the Minos transposase specifically in growing oocytes due to the use of a 6.5 Kb 5'flanking region and promoter of the ZP 3 gene (FIG. 6). In both of the Minos transposase (ZP3/ILMi) lines, the transgene integrated as a tandem array. In this example we used ZP3/I LMi line 15 with the higher number of copies integrated (data not shown). As expected, transposase expression in this line was restricted to the ovaries (FIG. 7). RT-PCR performed on RNA samples from different tissues of transgenic ZP3/ILMi line showed that the ~360 bp fragment, corresponding to the correctly spliced transposase RNA, was restricted to the ovary. The amplification of contaminating DNA to a similar sized fragment was prevented by using a primer which spans an exon/intron junction (beta globin IVSII-FIG. 6).

Since the Minos transposase expression from the transgene is driven by the ZP3 promoter, it should be expressed only in growing oocytes during a 2-to-3-week period of oogenesis.

Figure 8:
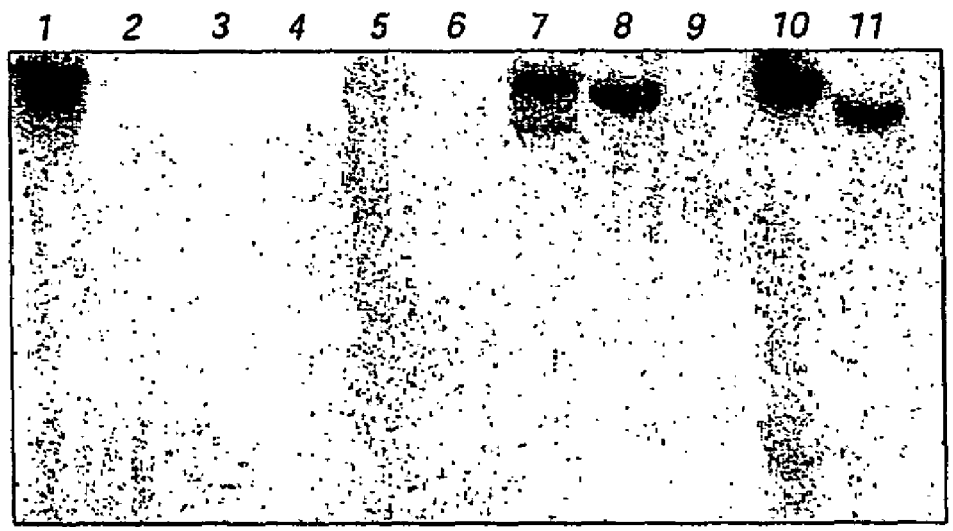
FIG. 8 illustrates Southern blot analysis of different offspring showing transposition events. All DNA samples were BglII digested and probed with a $^{32}P$ labelled GFP probe. Lane 1 is a control (female mouse carrying the GFP transposon as a multicopy on Chr 14 and expressing Minos transposase in developing oocytes). Lanes 2, 5, 6, 7, 8, 10 and 11 correspond to progeny of a double transgenic female and wt male. They all represent different transposition events. Lanes 2 and 5: mice with 2 transposition events. Lanes 3 and 4 correspond to the offspring of the mouse in lane 2 with 2 transposition events, showing segregation of the insertions (lane 3 on chromosome 2, lane 4 on chromosome 14 near the centromere). Lane 9: Offspring of the mouse shown in lane 8, showing segregation.

Normally, zona pellucida transcripts cannot be detected in primordial oocytes (10-15 em), and maximum levels are observed in 50 μm-diameter oocytes. As the oocytes reach maximum size (70-80 μm), the level of ZP3 transcripts begins to decline. Ovulated eggs contain less than 5% of the peak levels of all zona pellucida transcripts (Millar, et al. (1991) *Molecular and Cellular Biology* 11, 6197-6204; Liu, C et al. (1996) *Proc. Natl. Acad. Sci. USA.*, 5431-5436). To exclude the possibility that some transposase activity remains in mature oocytes to mediate transposition of a paternally contributed transposon transgene, the Zp3/ILMi males (that do not express the transposase) were mated to females of the multycopy transposon carrying line MCG. Female progeny positive for both transgenes were selected for further study. We analysed 307 progeny of the double positive females and wild type males by Southern blot analysis. EcoRV and/or BglII digested tail DNA was blotted and hybridised with the GFP probe. Since neither of these two enzymes cuts within the transposon, there is one single band that hybridises to the transposon probe in an MCG line. If transposition occurs and the transposon inserts outside the genomic EcoRV or BglII fragment where it was initially present, a new band will be detected after hybridisation with the transposon probe. Out of 307 mice, 146 mice were transposon (GFP) positive. Among these 146 mice, 12 transposition events were observed that resulted in a novel restriction fragment on the blot giving a transposition frequency of 8.2%. In two mice, two independent transposition events were found (FIG. 8 lanes 2 and 5). The observation that some offspring carry Minos mediated insertions but did not inherit the transposase transgene strongly suggests that transposition occurred in the germ cells of the mother prior to meiosis II.

To prove that the observed transposition events had indeed occurred in the germ line, animals with transposition events were further crossed to wild type mice. Analysis of their progeny showed that these mice stably transmitted the reinserted Minos element (FIG. 8). The segregation of a transposon concatemer and a new insertion into two different lines in the F1 generation was clear evidence that transposition had occurred to another chromosome (FIG. 8, lane 2 versus 3 and 4, and lane 8 versus 9). In all transposition events except one, a single copy of the transposon was mobilised.

It has been noted previously that the size of a transposon influences its transposition frequency; longer elements tend to transpose with a lower frequency (Lampe, D. J. et al (1998). *Genetics* 149, 179-187; Fischer, S. E., et al. (1999) *Mol. Gen. Genet.* 262, 268-274), suggesting that when transposase binding sites (inverted repeats) are closer to each other they are recognised more efficiently.

Figure 9:
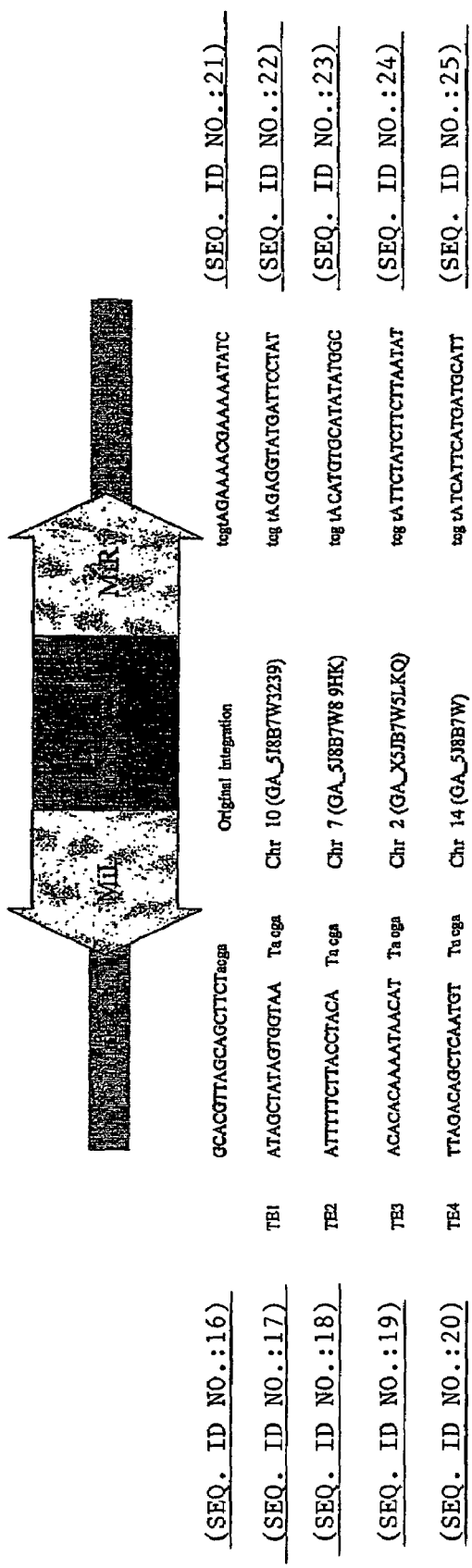
FIG. 9 illustrates the sequence of the parental and four different Minos insertions in the *Mus musculus* genome. Chromosomal sequences flanking the new inserted transposon are represented by capital letters, transposon sequence in small letters and the target site duplication in red. The chromosomal locations of insertions and scaffold numbers from the Celera database are indicated.
Figure 10:
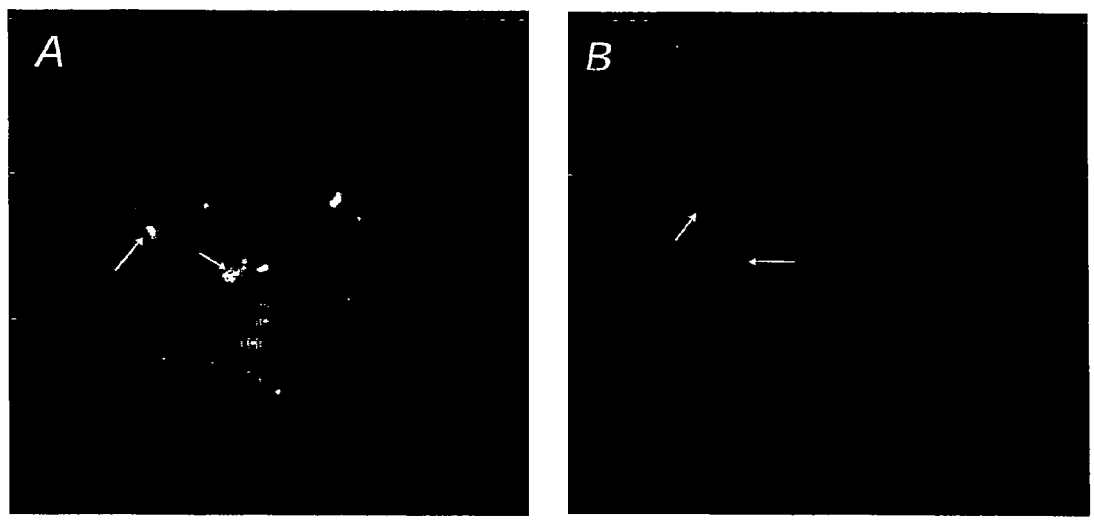
FIG. 10 illustrates FISH analysis of Minos transposition events. Chromosomes were stained with 4', 6-diamino-2-phenylindole and probed with a GFP probe as described in Example 4 Materials and Methods. Panel A: mouse 8218-01 with two transposition events (on chromosome 2 and at the centromere of chromosome 14; see FIG. 8 lane 2). Red colour (indicated by arrow head): staining after tyramide amplification (see Example 4 Materials and Methods). Panel B: mouse 8218-02 with two transposition events (one on chromosome 18 and one near the telomere of chromosome 14 close to the initial position of the transposon concatemer (FIG. 8 lane 5). Green colour (indicated by arrow head): FITC staining. Yellow arrows indicate transposition events.

Minos transpositions are characterised by a precise integration of the element without mobilisation of flanking DNA. In *Drosophila* and in HeLa cells, the transposon inserts into TA dinucleotide causing target site duplication upon insertion (17, 29). To investigate the structure of the insertions in the mouse genome, we cloned the flanking regions (as described in Materials and Methods) from five different transposition events. As is observed in *Drosophila*, the Minos ends were flanked by the diagnostic TA dinucleotide followed by sequences unrelated to the sequence that flanks the element in the founder mouse line MCG (FIG. 9). BLAST searches with the obtained sequences in the Celera mouse genome database showed that all five of the novel flanking sequences (in one case only one flanking sequence was obtained) correspond to widely scattered genomic locations (FIG. 9). Out of five transposition events analysed only one was on chromosome 14. It is a single copy of the transposon integrated into a centromeric region without the presence of a transposon concatamer on tip of chromosome 14. Thus this transposition event occurred into a different chromosome (See FIG. 10). The DNA Fluorescent in Situ Hybridisation (FISH analysis) performed on metaphase spreads from peripheral white blood cells confirmed the results obtained from sequencing of the flanking regions (data not shown). However, transposition events that were clearly detectable by Southern blot analysis but were located close to the original site on the same chromosome would not be identified by FISH. It is actually very difficult to detect single copy (3 kb) transpositions by FISH and this may partially explain the low frequency of transposition (0.61%) we obtained previously with the same transposon containing transgenic line (MCG) and Minos transposase expressed specifically in T cells (Zagoraiou, L., et al. (2001) *Proc. Natl. Acad. Sci. USA* 98, 11474-11478) where FISH was the only method of detection used. Since "local insertions", close to the original site of the element, are quite frequent at least with the *Drosophila* P element (Zhang, P.& Sprading, A. C. (1993) *Genetics* 133, 361-373) and *Sleeping Beauty* (Luo, G. et al. (1998) *Proc. Natl. Acad. Sci. USA.* 95, 10769-10773; Fisher, S. E. J., et al. (2001) *Proc. Natl. Acad. Sci. USA.* 98, 6759-6764), it is unlikely that this would not be the case with the Minos element.

In order to determine the size of the EcoRV/BglII flanking regions we generated a single copy transposon line from the MCG line using the loxP/Cre system (data not shown). On the basis of Southern blot data, there is approximately 10 kb of genomic sequence flanking the transposon, within the EcoRV and BglII diagnostic digests. Local reinsertions that occur within this area (but which are not interesting for mutagenesis purposes), will escape detection and are not included in our estimation of the frequency of transposition. Thus, the frequency of 8.2% represents the "useful" transposition frequency rather than the actual transposition frequency. The reported frequency of transpositions in the mouse male germ line with Sleeping Beauty was approximately 20%, but only 2% had transposed to a different chromosome (Fisher, S. E. J., Wienholds, E. & Plasterk, R. H. A. (2001) *Proc. Natl. Acad. Sci. USA.* 98, 6759-6764). In contrast we find for Minos approx. 6% transposition to a different chromosome (8 out of 11 analysed and 1 unknown, out of 146 offspring), while only 3 out of 11 transpositions were to the same chromosome (e.g. FIG. 10B). This suggests that the Minos system has a preference for transpositions to a different chromosome (provided there weren't many transpositions close to the original site that went undetected). It should be noted however that a direct comparison of the different transposon systems published to date may not be very valid. The size, the copy number and the initial chromosomal position of the transposon might all affect the transposition efficiency and none of these were comparable in the different systems.

In conclusion, these results show that transposition can be achieved in the mouse germ line and that, by selecting the time of induction, mobilisation of transposons may be induced at a predetermined stage of embryo development. Furthermore, the results demonstrate that systems using, for example, Minos, are excellent tools for insertional gene inactivation, gene tagging, enhancer trapping and exon trapping in organisms, for example, mice.

Example 6

Generation of Transgenic Progeny and Induction of Transposition Events

Transposition events were detected in the progeny of a cross between a double positive transposon/transposase transgenic male and a non-transgenic female.

Double positive transposon/transposase transgenic males were obtained by crossing Trap A or Trap B transgenic lines with an H1 t transposase knock in line (see FIG. 16). Trap A and Trap B transgenic lines were generated by means of transgenesis (injection of the DNA into fertilized mouse oocytes). The injected construct is depicted in FIG. 16. The Trap A line contains approximately 30 copies of the transposon (trap construct) integrated on chromosome 5 and the Trap B line has approximately 40 copies of the transposon integrated on chromosome 4. An H1 t knock in line was generated by blastocyst injection of ES cells whereby mousified Minos transposase (see FIG. 17) was targeted into the H1-t locus by homologous recombination, thereby ensuring sperm specific expression. Southern blotting demonstrated the correct ES clone (see FIG. 16). The resulting chimeras gave germ line transmission. The line was further bred to a Rosa FLP mouse to remove the puro gene. The targeting strategy and the removal of the Puro gene are presented in FIG. 16.

Figure 18:
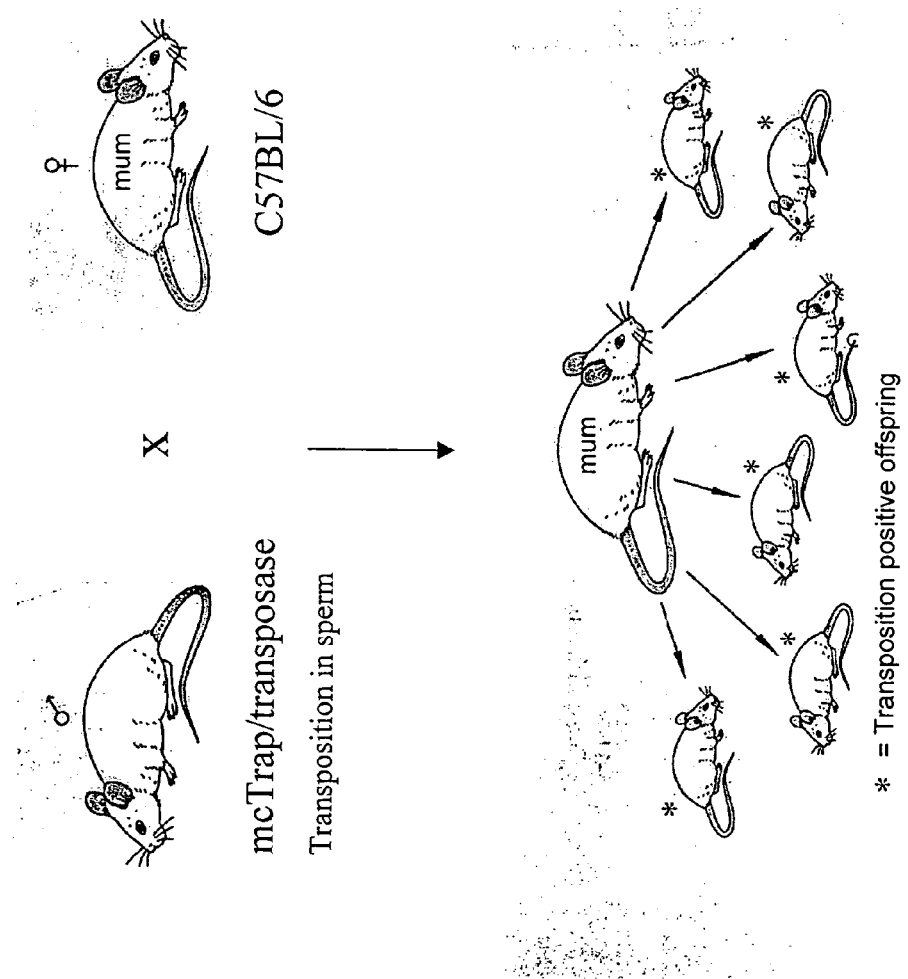
FIG. 18 depicts one embodiment of a breeding scheme according to the invention. According to this embodiment, the male contributes both the transposon and the transposase.

Transposition positive offspring were produced by crossing the double positive transposon/transposase transgenic males (described above) with non-transgenic females, as depicted in FIG. 18. Transposition events occurred in the sperm.

Figure 19:
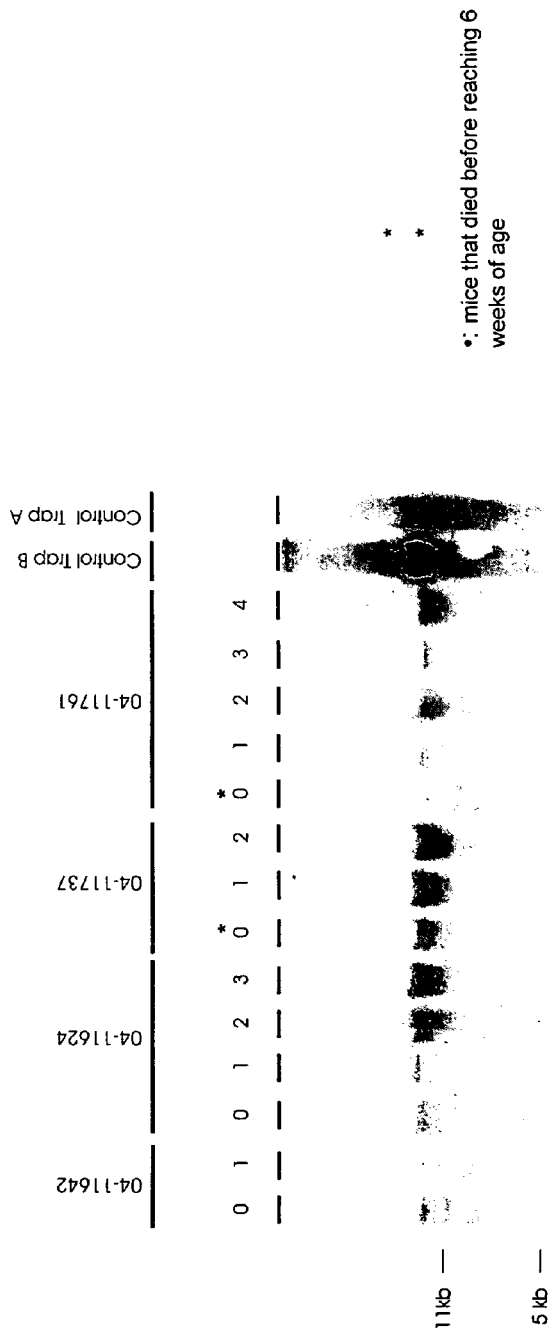
FIG. 19 is a Southern blot showing transposition events.
Figure 20:
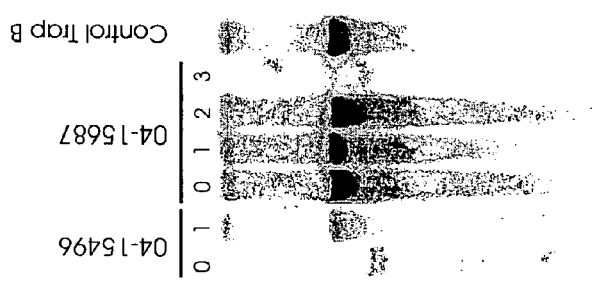
FIG. 20 is a Southern blot showing transposition events.
Figure 22:
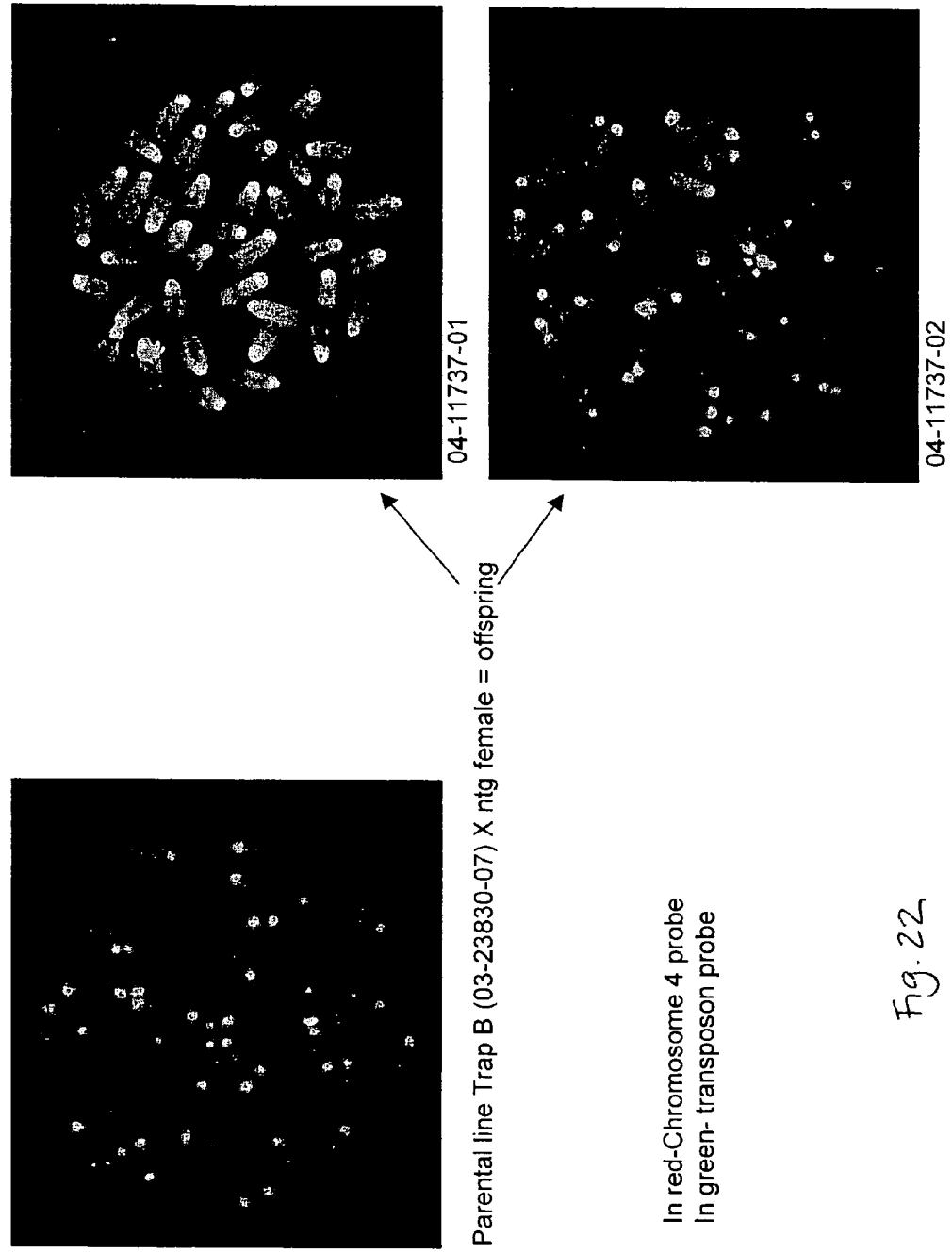
FIG. 22 shows the results of FISH analysis of transposition events.

FIGS. 19 and 20 are Southern blot analyses showing transposition events in litters 04-11642 and 04-11761 (produced by breeding a non-transgenic female with male 03-23712-05 (transgenic for Trap A and transposase)); litters 04-11624 and 04-11737 (produced by breeeding a non-transgenic female with male 03-23830-07 (transgenic for Trap B and transposase)); and litters 04-12496 and 04-15687 (produced by breeding a non-transgenic female with male 03-23830-07 (transgenic for Trap B and transposase). The results of FISH analysis of Minos transposition events are presented in FIGS. 21 and 22.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are apparent to those skilled in molecular biology or related fields are intended to be within the scope of the following claims.

The invention claimed is:

1. A method of generating a transgenic mouse comprising novel transposition events in its genome by inducing gene transposition in the developing spermatocyte, comprising the steps of:
   a) generating a first adult transgenic mouse comprising within its genome one or more copies of a Tc/1 mariner transposon;
   b) generating a second adult transgenic mouse comprising within its genome one or more copies of a gene encoding a transposase cognate for said transposon, wherein said transposase is operably linked to H1t regulatory sequences such that said gene encoding said transposase is expressed only in the developing spermatocyte;
   c) crossing said first adult transgenic mouse with said second adult transgenic mouse to provide a first generation, male progeny which comprises, both (i) one or more copies of said transposon and (ii) one or more copies of said gene encoding said transposase cognate for said transposon, wherein said transposase is operably linked to H1t regulatory sequences such that said gene encoding said transposase is expressed only in the developing spermatocyte;
   d) expressing said gene encoding said transposase in said first generation male progeny to mobilize said transposon within the developing spermatocyte;
   e) crossing said first generation male progeny with a female, to generate second generation progeny comprising at least one transposition event within their genome; and
   f) identifying said transgenic second generation progeny comprising mouse progeny.

2. The method of claim 1, wherein said first and second transgenic mice are generated by oocyte injection.

3. The method of claim 1, wherein one or both of said first and second transgenic mice are generated from ES cells.

4. The method according to claim 1, where said transgenic mouse is derived from a genetic background predisposed to a disease state.

5. The method according to claim 1, wherein said transposon and/or the gene encoding said transposase are located within a chromatin opening element such that said transposon and/or said gene encoding said transposase are located in open chromatin structure.

6. The method according to claim 5 wherein said chromatin opening element is a ubiquitously-acting chromatin opening element (UCQE), a locus control region (LCR), a CpG island or an insulator.

7. The method according to claim 1, wherein expression of said gene encoding said transposase is eliminated by gene excision as a result of or after mobilisation of said transposon.

8. The method according to claim 1, wherein said transposon and/or the gene encoding said transposase is inserted into or adjacent to an expressed gene.

9. The method according to claim 1, wherein said transposon is Minos, mariner, Hermes, piggyBac or Sleeping Beauty.

10. The method according to claim 1, wherein said transposon has been modified to include a heterologous nucleic acid sequence, flanked by inverted terminal repeats homologous to said transposon.

11. The method according to claim 1, wherein the nucleotide sequence of said gene encoding said transposase has been modified to optimise mammalian codon usage.

12. A method for detecting the position of a transposed transposon in a transgenic mouse second generation progeny wherein said transposed transposon is associated with a change in the phenotype of said second generation progeny as compared to the parental line, comprising:
    (a) generating a second generation progeny comprising at least one transposition event within their genome, according to the method of claim 1;
    (b) detecting the position of said at least one transposition event in the genome of said second generation progeny;
    (c) identifying in said second generation progeny said change in the phenotype of said second generation progeny as compared to the parental lines;
    (d) correlating the position of said transposition event(s) with the change in phenotype, wherein the position of the transposition event(s) indicates the location of one or more genetic loci associated with said change in the phenotype of the second generation progeny as compared to the parental lines; and
    (e) cloning said one or more genetic loci; and
    (f) identifying said position of said insertional event within or adjacent to a gene.

13. A method for isolating a gene which is correlated with a phenotypic characteristic in a transgenic mouse comprising the steps of:
    (a) generating a second generation progeny comprising at least one transposition event within their genome, according to the method of claim 1;
    (b) detecting the position of said at least one transposition event in said genome of said second generation progeny;
    (c) identifying in said second generation progeny the presence of a plurality of cells displaying said phenotypic characteristic; and
    (d) cloning the genetic loci comprising said transposition event.

14. A method of generating a transgenic mouse having a plurality of cells or tissues homogeneous for a gene modified by transposon mobilisation, the method comprising generating a transgenic spermatocyte and inducing transposition according to the method of claim 1.

15. A method for detecting and characterizing an insertional mutation in a second generation transgenic mouse offspring wherein said second generation transgenic mouse offspring has a change in a phenotype as compared to the parental lines, comprising the steps of:
    (a) generating a second generation transgenic mouse offspring carrying at least one or more transposon transposition event by the method according to claim 1;
    (b) detecting the position of said one or more transposon transposition events in the genome of said second generation transgenic mouse offspring;
    (c) identifying a second generation transgenic mouse offspring comprising a change in a phenotype as compared to the parental lines;
    (d) correlating the position of said one or more transposition events with the observed variant phenotype, the position of the one or more transposition events being indicative of the location of one or more genetic loci associated with the observed change in the phenotype of said second generation transgenic mouse offspring as compared to the parental lines; and
    (e) cloning the genetic loci wherein said transposition has inserted and identifying the position of the insertional event within or adjacent to a gene.

16. The method of claim 15, wherein said second generation transgenic mouse offspring comprises a tumor.

17. The method of claim 15, wherein detecting the position of said one or more transposition events comprises determining the nucleotide sequences adjacent to the mobilized transposon.

18. The method of claim 16, wherein the locations of a plurality of mobilized transposons are identified in the genomic DNA of a tumor cell.

19. The method of claim 15, wherein step (c) and/or step (e) is performed prior to step (b).

* * * * *